United States Patent
Dean et al.

(10) Patent No.: US 6,867,017 B1
(45) Date of Patent: Mar. 15, 2005

(54) ATP-BINDING TRANSPORTER (ABC7) AND METHODS FOR DETECTION OF ANEMIA AND ATAXIA

(75) Inventors: Michael Dean, Frederick, MD (US); Rando Allikmets, Monroe, NY (US); Amy Ann Hutchinson, Fort Lee, NJ (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/422,840

(22) Filed: Oct. 21, 1999

Related U.S. Application Data

(60) Provisional application No. 60/105,497, filed on Oct. 23, 1998.

(51) Int. Cl.[7] .......................... C12N 15/12; C12N 15/63; C12N 5/00; C07K 14/00; C07H 21/04
(52) U.S. Cl. .................... 435/69.1; 435/320.1; 435/325; 435/6; 530/350; 536/23.5
(58) Field of Search .............................. 435/69.1, 320.1, 435/325, 6; 530/350; 536/23.5

(56) References Cited

FOREIGN PATENT DOCUMENTS

WO    WO 9401548    *    1/1994

OTHER PUBLICATIONS

Savary et al. Isolation and chromosomal mapping of a novel ATP–binding cassette transporter conserved in mouse and human Genomics 41 (2), 275–278 (1997).*

Stratagene Catalog 1988, p. 39.*

Stratagene Catalog 1991, p. 66.*

Hillier et al. zv65c05.r1 Soares_total_fetus_Nb2HF8_9w Homo sapiens cDNA clone IMAGE:758504 5' similar to TR:G1167982 G1167982 ABC Transporter–7; mRNA sequence. (1997).*

Adams et al. EST176101 Colon carcinoma (Caco–2) cell line II Homo sapiens cDNA 5' end, mRNA sequence. (1997).*

Savary, S., et al., *"Isolation and Chromosomal Mapping of a Novel ATP–Binding Cassette Transporter Conserved in Mouse and Human"* GENOMICS, vol. 41 (1997) pp. 275–278.

Kispal, G., et al., *"The ABC transporter Atm1p is required for mitochondrial iron homeostasis,"* FEBS Letters, vol. 418 (1997) pp. 346–350.

Raskind, W., et al., *"X–linked Sideroblastic Anemia and Ataxia: Linkage to Phosphoglycerate Kinase at Xq13,"* Am. J. Hum. Genet., vol. 48 (1991) pp. 335–341.

* cited by examiner

*Primary Examiner*—Yvonne Eyler
*Assistant Examiner*—Joseph F. Murphy
(74) *Attorney, Agent, or Firm*—Klarquist Sparkman, LLP.

(57) ABSTRACT

Disclosed is a novel ATP-binding cassette gene (ABC7), polypeptide and methods of detecting mutations therein. Further, the disclosure provides methods of detecting ABC7 associated disease and treatments thereof. In particular, the disclosure provides methods of detecting X-linked Sideroblastic Anemia and Ataxia associated with a mutation in the ABC7 polypeptide.

23 Claims, 5 Drawing Sheets

```
         1
       +         +              + + +              +
ABC7   MHSWRWAAAA AAFEKRRHSA ILIRPLVSVS GSGPQWRPHQ LGALGTARAY
Atm1p  MLLLPRCPVI GRIVRSKFRS GLIRNHSPVI .......... ..........
       +     +    +   + + +      +
         51
ABC7   QIPESLKSIT WQRLGKGNSG QFLDAAKALQ VWPLIEKRTC WHGHACGGLH
Atm1p  .FTVSKLSTQ RPLLFNSAVN LWNQAQKDIT HKKSVEQFSS APKVKTQVKK

101
ABC7   TDPKEGLKDV DTRKIIKAML SYVWPKDRPD LRARVAISLG FLGGAKAMNI
Atm1p  TSKAPTLSEL ...KILKDLF RYIWPKGNNK VRIRVLIALG LLISAKILNV
                                            ‾‾‾‾‾ ‾‾‾‾‾‾‾‾‾‾
                                                      TM1
         151
ABC7   VVPFMFKYAV DSLNQMSGNM LNLSDAPNTV ATMATAVLIG YGVSRAGAAF
Atm1p  QVPFFFKQTI DSMN...... IAWDDPTVAL PAAIGLTILC YGVARFGSVL
       ‾‾‾‾‾‾                          ‾‾‾‾‾‾‾‾‾‾ ‾‾‾‾‾‾‾‾‾‾
                                                      TM2
         201
ABC7   FNEVRNAVFG KVAQNSIRRI AKNVFLHLHN LDLGFHLSRQ TGALSKAIDR
Atm1p  FGELRNAVFA KVAQNAIRTV SLQTPQHLMK LDLGWHLSRQ TGGLTRAMDR
       ‾

251
ABC7   GTKGISFVLS ALVFNLLPIM FEVMLVSGVL YYKCGAQFAL VTLGTLGTYT
Atm1p  GTKGISQVLT AMVFHIIPIS FEISVVCGIL TYQFGASFAA ITFSTMLLYS
              ‾‾‾ ‾‾‾‾‾‾‾‾‾‾                      ‾‾‾‾‾‾‾‾‾‾
                    TM3                               TM4
         301
ABC7   APTVA V TRW RTRFRIEMNK ADNDAGNAAI DSLLNYETVK YFNNERYEAQ
Atm1p  IFTI.KTTAW RTHFRRDANK ADNKAASVAL DSLINFEAVK YFNNEKYLAD
       ‾‾‾‾

350                                           *
ABC7   RYDGFLKTYE TASLKSTSTL AMLNFGQSAI FSVGLTAIMV LASQGIVAGT
Atm1p  KYNGSLMNYR DSQIKVSQSL AFLNSGQNLI PTTALTAMMY MGCTGVIGGN
                                    ‾‾ ‾‾‾‾‾‾‾‾‾‾
                                          TM5
         400
ABC7   LTVGDLVMVN GLLFQLSLPL NFLGTVYRET RQALIDMNTL FTLLKVDTQI
Atm1p  LTVGDLVLIN QLVFQLSVPL NFLGSVYRDL KQSLIDMETL FKLRKNEVKI
                 ‾‾‾‾‾‾‾‾‾‾
                    TM6
         450
ABC7   KDKVMASPLQ ITPQTA.TVA FDNVHFEYIE GQKVLSGISF EVPAGKKVAI
Atm1p  KN..AERPLM LPENVPYDIT FENVTFGYHP DRKILKNASF TIPAGWKTAI

499
ABC7   VGGSGSGKST IVRLLFRFYE PQKGSIYLAC QNIQDVSLES LRRAVGVVPQ
Atm1p  VGSSGSGKST ILKLVFRFYD PESGRILING RDIKEYDIDA LRKVIGVVPQ
           Walker A
         549
ABC7   DAVLFHNTIY YNLLYGNISA SPEEVYAVAK LAGLHDAILR MPHGYDTQVG
Atm1p  DTPLFNDTIW ENVKFGRIDA TDEEVITVVE KAQLAPLIKK LPQGFDTIVG 599
ABC7   ERGLKLSGGE KQRVAIARAI LKDPPVILYD EATSSLDSIT EETILGAMKD
Atm1p  ERGLMISGGE KQRLAIARVL LKNARIMFFD EATSALDTHT EQALLRTIRD
              C                                Walker B
         649
ABC7   VVK..HRTSI FIAHRLSTVV DADEIIVLDQ GKVAERGTHH GLLANPHSIY
Atm1p  NFTSGSRTSV YIAHRLRTIA DADKIIVLDN GRVREEGKHL ELLAMPGSLY 697
ABC7   SEMWHTQSSR VQNHDNPKWE AKKENISKEE ERKKLQEEIV NSVKGCGNCSC*
Atm1p  RELWTIQ... .......... ...EDLDHLE NELKDQQEL*
```

FIGURE 1A

```
   1  ATGGCGCTGC TCGCGATGCA TTCTTGGCGC TGGGCGGCCG CGGCGGCTGC
  51  TTTCGAAAAG CGCCGGCACT CCGCGATTCT GATCCGGCCT TTAGTCTCTG
 101  TTAGCGGCTC AGGTCCGCAG TGGAGGCCAC ATCAACTCGG CGCCTTGGGA
 151  ACCGCTCGAG CCTACCAGAT TCCAGAGTCA TTAAAAAGTA TCACATGGCA
 201  GAGATTGGGA AAAGGCAATT CAGGACAGTT CTTAGATGCT GCAAAGGCTC
 251  TCCAGGTATG GCCACTGATA GAAAGAGGA CATGTTGGCA TGGTCATGCA
 301  GGAGGAGGAC TCCACACAGA CCCAAAAGAA GGGTTAAAAG ATGTTGATAC
 351  TCGGAAAATC ATAAAAGCAA TGCTTTCTTA TGTGTGGCCC AAAGACAGGC
 401  CAGATCTACG AGCTAGAGTT GCCATTTCGC TGGGATTTTT GGTGGTGCA
 451  AAGGCCATGA ATATTGTGGT TCCCTTCATG TTTAAATATG CTGTAGACAG
 501  CCTCAACCAG ATGTCGGGAA ACATGCTGAA CCTGAGTGAT GCACCAAATA
 551  CAGTTGCAAC CATGGCAACA GCAGTTCTGA TTGGCTATGG TGTATCAAGA
 601  GCTGGAGCTG CTTTTTTTAA CGAAGTTCGA AATGCAGTAT TTGGCAAGGT
 651  AGCCCAGAAT TCAATCCGAA GAATAGCCAA AAATGTCTTT CTCCATCTTC
 701  ACAACCTGGA TCTGGGTTTT CACCTGAGCA GACAGACGGG AGCTTTATCT
 751  AAGGCTATTG ACAGAGGAAC AAAGGGTATC AGTTTTGTCC TGAGTGCTTT
 801  GGTATTTAAT CTTCTTCCCA TCATGTTTGA AGTGATGCTT GTCAGTGGTG
 851  TTTTGTATTA CAAATGCGGT GCCCAGTTTG CTTTGGTAAC CCTTGGAACA
 901  CTTGGTACAT ACACAGCATT CACAGTTGCA GTCACACGGT GGAGAACTAG
 951  ATTTAGAATA GAAATGAACA AAGCAGATAA TGATGCAGGT AATGCTGCTA
1001  TAGACTCACT GCTGAATTAT GAAACTGTGA AGTATTTAA TAATGAAAGA
1051  TATGAAGCAC AGAGATATGA TGGATTTTTG AAGACGTATG AGACTGCTTC
1101  ATTGAAAAGT ACCTCTACTC TGGCTATGCT GAACTTTGGT CAAAGTGCTA
1151  TTTTCAGTGT CGGTTTAACA GCTATAATGG TGCTCGCCAG TCAGGGAATT
1201  GTGGCAGGTA CCCTTACTGT TGGAGATCTA GTAATGGTGA ATGGACTGCT
1251  TTTTCAGCTT TCATTACCCC TGAACTTTCT GGGAACTGTA TATAGAGAGA
1301  CTAGACAAGC ACTCATAGAT ATGAACACCT TGTTTACTCT ACTCAAGGTA
1351  GACACCCAAA TTAAAGACAA AGTGATGGCA TCTCCCCTTC AGATCACACC
1401  ACAGACAGCT ACCGTGGCCT TTGATAATGT GCATTTTGAA TACATTGAGG
1451  GCCAGAAAGT CCTTAGTGGA ATATCCTTTG AAGTCCCTGC AGGAAAGAAA
1501  GTGGCCATTG TAGGAGGTAG TGGGTCAGGG AAAAGCACAA TAGTGAGGCT
1551  ATTATTTCGC TTCTATGAGC CTCAAAAGGG TAGCATTTAT CTTGCTGGTC
1601  AAAATATACA AGATGTGAGC CTGGAAAGCC TTCGGAGGGC AGTGGGAGTG
1651  GTACCTCAGG ATGCTGTCCT CTTCCATAAT ACTATTTATT ACAACCTCTT
1701  ATATGGAAAC ATCAGTGCTT CACCTGAGGA AGTGTATGCA GTGGCAAAAT
1751  TAGCTGGACT TCATGATGCA ATTCTTCGAA TGCCACATGG ATATGACACC
1801  CAAGTAGGGG AACGAGGACT CAAGCTTTCA GGAGGAGAAA AGCAAAGAGT
1851  AGCAATTGCA AGAGCCATTT TGAAGGACCC CCAGTCATA CTCTATGATG
1901  AAGCTACTTC ATCGTTAGAT TCGATTACTG AAGAGACTAT TCTTGGTGCC
1951  ATGAAGGATG TGGTCAAACA CAGAACTTCT ATTTTCATTG CACACAGATT
2001  GTCAACAGTG GTTGATGCAG ATGAAATCAT TGTCTTGGAT CAGGGTAAGG
2051  TAGCCGAACG TGGTACCCAC CATGGTTTGC TTGCTAACCC TCATAGTATC
2101  TATTCAGAAA TGTGGCATAC ACAGAGCAGC CGTGTGCAGA ACCATGATAA
2151  CCCCAAATGG GAAGCAAAGA AAGAAAATAT ATCCAAAGAG GAGGAAAGAA
2201  AGAAACTACA AGAAGAAATT GTCAATAGTG TGAAAGGCTG TGGAAACTGT
2251  TCGTGCTAAG TCACATAAGA CATTTTCTTT TTTTGTTGTT TTGGACTACA
2301  TATTTGCACT GAAGCAGAAT TGTTTTATTA AAAAAATCAT ACATT
```

FIGURE 1B

```
1     ATGGCGCTGC  TCGCGATGCA  TTCTTGGCGC  TGGGCGGCCG  CGGCGGCTGC
51    TTTCGAAAAG  CGCCGGCACT  CCGCGATTCT  GATCCGGCCT  TTAGTCTCTG
101   TTAGCGGCTC  AGGTCCGCAG  TGGAGGCCAC  ATCAACTCGG  CGCCTTGGGA
151   ACCGCTCGAG  CCTACCAGAT  TCCAGAGTCA  TTAAAAAGTA  TCACATGGCA
201   GAGATTGGGA  AAAGGCAATT  CAGGACAGTT  CTTAGATGCT  GCAAAGGCTC
251   TCCAGGTATG  GCCACTGATA  GAAAAGAGGA  CATGTTGGCA  TGGTCATGCA
301   GGAGGAGGAC  TCCACACAGA  CCCAAAAGAA  GGGTTAAAAG  ATGTTGATAC
351   TCGGAAAATC  ATAAAAGCAA  TGCTTTCTTA  TGTGTGGCCC  AAAGACAGGC
401   CAGATCTACG  AGCTAGAGTT  GCCATTTCGC  TGGGATTTTT  GGGTGGTGCA
451   AAGGCCATGA  ATATTGTGGT  TCCCTTCATG  TTTAAATATG  CTGTAGACAG
501   CCTCAACCAG  ATGTCGGGAA  ACATGCTGAA  CCTGAGTGAT  GCACCAAATA
551   CAGTTGCAAC  CATGGCAACA  GCAGTTCTGA  TTGGCTATGG  TGTATCAAGA
601   GCTGGAGCTG  CTTTTTTTAA  CGAAGTTCGA  AATGCAGTAT  TTGGCAAGGT
651   AGCCCAGAAT  TCAATCCGAA  GAATAGCCAA  AAATGTCTTT  CTCCATCTTC
701   ACAACCTGGA  TCTGGGTTTT  CACCTGAGCA  GACAGACGGG  AGCTTATCT
751   AAGGCTATTG  ACAGAGGAAC  AAAGGGTATC  AGTTTGTCC   TGAGTGCTTT
801   GGTATTTAAT  CTTCTTCCCA  TCATGTTTGA  AGTGATGCTT  GTCAGTGGTG
851   TTTTGTATTA  CAAATGCGGT  GCCCAGTTTG  CTTTGGTAAC  CCTTGGAACA
901   CTTGGTACAT  ACACAGCATT  CACAGTTGCA  GTCACACGGT  GGAGAACTAG
951   ATTTAGAATA  GAAATGAACA  AAGCAGATAA  TGATGCAGGT  AATGCTGCTA
1001  TAGACTCACT  GCTGAATTAT  GAAACTGTGA  AGTATTTTAA  TAATGAAAGA
1051  TATGAAGCAC  AGAGATATGA  TGGATTTTTG  AAGACGTATG  AGACTGCTTC
1101  ATTGAAAAGT  ACCTCTACTC  TGGCTATGCT  GAACTTTGGT  CAAAGTGCTA
1151  TTTTCAGTGT  CGGTTTAACA  GCTATAATGG  TGCTCGCCAG  TCAGGGAATG
1201  GTGGCAGGTA  CCCTTACTGT  TGGAGATCTA  GTAATGGTGA  ATGGACTGCT
1251  TTTTCAGCTT  TCATTACCCC  TGAACTTTCT  GGGAACTGTA  TATAGAGAGA
1301  CTAGACAAGC  ACTCATAGAT  ATGAACACCT  TGTTTACTCT  ACTCAAGGTA
1351  GACACCCAAA  TTAAAGACAA  AGTGATGGCA  TCTCCCCTTC  AGATCACACC
1401  ACAGACAGCT  ACCGTGGCCT  TTGATAATGT  GCATTTGAA   TACATTGAGG
1451  GCCAGAAAGT  CCTTAGTGGA  ATATCCTTTG  AAGTCCCTGC  AGGAAAGAAA
1501  GTGGCCATTG  TAGGAGGTAG  TGGGTCAGGG  AAAAGCACAA  TAGTGAGGCT
1551  ATTATTTCGC  TTCTATGAGC  CTCAAAAGGG  TAGCATTTAT  CTTGCTGGTC
1601  AAAATATACA  AGATGTGAGC  CTGGAAAGCC  TTCGGAGGGC  AGTGGGAGTG
1651  GTACCTCAGG  ATGCTGTCCT  CTTCCATAAT  ACTATTTATT  ACAACCTCTT
1701  ATATGGAAAC  ATCAGTGCTT  CACCTGAGGA  AGTGTATGCA  GTGGCAAAAT
1751  TAGCTGGACT  TCATGATGCA  ATTCTTGAA   TGCCACATGG  ATATGACACC
1801  CAAGTAGGGG  AACGAGGACT  CAAGCTTTCA  GGAGGAGAAA  AGCAAAGAGT
1851  AGCAATTGCA  AGAGCCATTT  TGAAGGACCC  CCCAGTCATA  CTCTATGATG
1901  AAGCTACTTC  ATCGTTAGAT  TCGATTACTG  AAGAGACTAT  TCTTGGTGCC
1951  ATGAAGGATG  TGGTCAAACA  CAGAACTTCT  ATTTTCATTG  CACACAGATT
2001  GTCAACAGTG  GTTGATGCAG  ATGAAATCAT  TGTCTTGGAT  CAGGGTAAGG
2051  TAGCCGAACG  TGGTACCCAC  CATGGTTTGC  TTGCTAACCC  TCATAGTATC
2101  TATTCAGAAA  TGTGGCATAC  ACAGAGCAGC  CGTGTGCAGA  ACCATGATAA
2151  CCCCAAATGG  GAAGCAAAGA  AAGAAAATAT  ATCCAAAGAG  GAGGAAAGAA
2201  AGAAACTACA  AGAAGAAATT  GTCAATAGTG  TGAAAGGCTG  TGGAAACTGT
2251  TCGTGCTAAG  TCACATAAGA  CATTTCTTT   TTTTGTTGTT  TTGGACTACA
2301  TATTTGCACT  GAAGCAGAAT  TGTTTTATTA  AAAAAATCAT  ACATT
```

ATP-BINDING TRANSPORTER (ABC7) AND METHODS FOR DETECTION OF ANEMIA AND ATAXIA

This application claims the benefit under 35 U.S.C. §119 of prior U.S. provisional application No. 60/105,497, filed Oct. 23, 1998.

FIELD OF THE INVENTION

This invention relates to polynucleotides encoding ATP-Binding Transporter-7 (ABC7), polypeptides encoded by such polynucleotides, the use of such polynucleotides and polypeptides for detecting anemia and ataxia, as well as the production and isolation of such polynucleotides and polypeptides.

BACKGROUND OF THE INVENTION

The mitochondrion serves a central role in cellular iron metabolism. It is the, site of the final step of heme biosyntheses, addition of $Fe^{2+}$ to protoporphyrin, and contains a large amount of non-heme iron in the iron sulfur centers of the electron transport chain. In spite of its importance for normal mitochondrial function, very few human disorders have been described which result from abnormalities in mitochondrial iron homeostasis.

Sideroblastic anemias are a heterogenous group of disorders, characterized by hypochromic microcytic erythrocytes and iron accumulation in the mitochondria of bone marrow erythrocyte precursors. The disorder can be both acquired or inherited, and the mode of transmission may be mitochondrial, autosomal or X-linked.

The ATP-binding cassette (ABC) superfamily of transporters contains conserved in evolution proteins involved in energy-decedent transport of a wide variety of substrates across cell membranes, including those of organelles such as the mitochondria, peroxisomes and endoplasmic reticulum. Many ABC genes have been implicated in different inherited diseases, including cystic fibrosis, adrenoleukodystrophy and a number of retinal dystrophies.

A recent study by Savary et al., (Genomics (1997) 41:275–278), reports genomic mapping of the ATP binding cassette-7 (ABC7) in mouse and humans. Savary et al also provides a partial sequence related to human ABC7 and its alignment with the yeast and murine ABC7 protein to identify conserved sequences. In this study the gene encoding human ABC7 was mapped to the Xq12–q13 region of the human genome. Additionally, a study by Shimada et al., (J. Hum. Genet. 43(2), 115–122 (1998)) describes the cloning of hABC7 having GenBank assession no. AB005289.

The mitochondrial ABC protein (Atm1p), encoded by the ATM1 gene has been, described in yeast and found to be essential for the cell growth and maintenance of mitochondrial DNA. Yeast strains, deficient for the ATM1 gene, have been shown to accumulate high levels of iron in mitochondria.

SUMMARY OF THE INVENTION

The present invention is based on the discovery and cloning of the mitochondrial-specific ATP-binding cassette-7 (ABC7) gene, which is expressed in a number of cells and tissues including heart, skeletal muscle, pancreas, lung, liver, and placenta. Certain alterations in the ABC7 gene or its protein product result in ABC7-associated disorders, such as X-linked Sideroblastic anemia and ataxia (XLSA/A). The inventors have identified a mutant of wild type ABC7 associated with XLSA/A. This mutant includes a mutation at amino acid residue number 395 (isoleucine 395 to methionine; I395M (see FIG. 1)) in ABC7 polypeptide.

In a first embodiment, substantially purified wild type ABC7 (wtABC7) and mutant ABC7 (mtABC7) polypeptides and isolated polynucleotides encoding these polypeptides are provided. Antibodies which bind to these polypeptides are also disclosed.

In another embodiment, a method of diagnosis a subject having or at risk of having an ABC7-associated disorder is also provided. The method includes detecting an ATP-binding transporter-7 (ABC7) polypeptides by contacting a sample with an antibody that binds to the an ABC7 polypeptide. In another embodiment, the method includes detecting an ABC7 polynucleotide by contacting a sample with a nucleic acid probe that hybridizes to an ABC7 polynucleotide.

In yet another embodiment, the invention provides a method for detecting the presence of X-linked Sideroblastic Anemia and Ataxia (XLSA/A). The method includes contacting a sample from a subject with a reagent that detects the presence of a polypeptide having an I395M mutation in the ABC7 polypeptide.

In another embodiment, the invention provides a method for detecting X-linked Sideroblastic Anemia and Ataxia (XLSA/A) in a subject. The method includes contacting a sample from a subject with a reagent which detects the presence of a polynucleotide encoding an I395M polypeptide mutation of ABC7.

In another embodiment the invention provides a method for detecting an allele for X-linked Sideroblastic Anemia and Ataxia. The method includes contacting a sample from a subject with a reagent which detects the presence of a polynucleotide as set forth in SEQ ID NO:3.

In a further embodiment, a kit useful for detecting the presence of ABC7 polypeptide in a sample from a subject having an ABC7-associated disorder is provided. A kit useful for the detection of polynucleotides encoding ABC7 in a subject having an ABC7-associated disorder is also provided.

A method of delivery and expression of an ABC7 polynucleotide to a subject by transfecting a cell with a polynucleotide encoding ABC7 such that the cell expresses ABC7 is also provided.

A further embodiment provides a method of determining the diagnosis or prognosis of a subject having a sideroblastic anemia and ataxia. The method includes determining the level of a mutant ABC7 polypeptide in cells of the patient and correlating the level with diagnosis or prognosis of the patient.

BRIEF DESCRIPTION OF THE DRAWINGS

FIG. 1A shows the amino acid sequence of the ABC7 protein (SEQ ID NO:2) and alignment with the yeast Atm1p (SEQ ID NO:6). The predicted protein sequence is shown in one-letter amino acid code. Transmembrane domains predicted by hydropathy plot are underlined, designated TM and numbered, the Walker A and B motifs and the Signature motif C are in bold type, and the termination codon is indicated with an asterisk. The basic, positively charged residues of the putative mitochondrial targeting signal are marked by a+. The location of the I395M missense mutation is shown above the sequence (SEQ ID NO:4).

FIG. 1B shows the nucleic acid sequence of wildtype hABC7 (SEQ ID NO:1).

FIG. 1C shows the nucleic acid sequence of the mutant hABC7 (SEQ ID NO:3), which has a mutation at base pair 1200 wherein base 1200 is changed from T to G giving rise to the I395M mutation.

DESCRIPTION OF THE PREFERRED EMBODIMENTS

Figure 2:
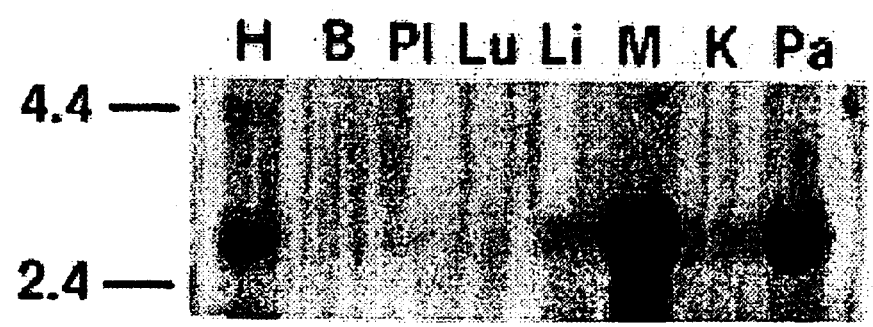
FIG. 2 shows the relative expression of ABC7 in human tissues. A fragment of the ABC7 cDNA clone was hybridized to a blot containing mRNA from heart (H), brain (B), placenta (Pl), lung (Lu), liver (Li), skeletal muscle (M), kidney (K) and pancreas (Pa).

This is the first disclosure of the complete full length ABC 7 sequence. Savary et al. (supra) describes sequences for an ABC7 polypeptide beginning essentially with the sixth transmembrane region (i.e., amino acid residues 408 to 747 of ABC7). The present invention discloses the entire amino acid sequence of the ABC7 polypeptide and the entire polynucleotide sequence encoding the ABC7 polypeptide. Based on the discovery of the complete amino acid and polynucleotide sequence of ABC7, the inventors were able to identify a previously unidentified mutation found in the fifth transmembrane region. The mutant polypeptide, referred to as having an I395M alteration, is associated with X-linked Sideroblastic Anemia and Ataxia (XLSA/A). The present invention relates to ABC7 and to the use of ABC7 antibodies, nucleic acid sequences, and amino acid sequences in the study, diagnosis, prognosis, and treatment of ABC7-associated disorders, including XLSA/A.

POLYNUCLEOTIDES AND POLYPEPTIDES

In one embodiment the invention provides substantially purified wild type ABC7 polypeptide (wtABC7). An exemplary wtABC7 polypeptide of the invention has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify wtABC7 using standard techniques for protein purification. The substantially pure polypeptide will yield a single major band oh a non-reducing polyacrylamide gel. The purity of the wtABC7 polypeptide can also be determined by amino-terminal amino acid sequence analysis.

Minor modifications of the wtABC7 primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein so long as the biological activity of the wtABC7 still exists. For example, an in frame addition of glutamine at position 50 results in a protein which has the same biological activity as wtABC7.

In addition, the present invention provides a substantially pure mutant ABC7 polypeptide (mtABC7). An exemplary mtABC7 has an amino acid sequence as set forth in SEQ ID NO:4. The mtABC7 of SEQ ID NO:4 has an amino acid sequence which differs from the wtABC7 of SEQ ID NO:2 at amino acid number 395, wherein the amino acid has been changed from isoleucine to methionine in the fifth transmembrane domain. This mtABC7 is a naturally occurring mutant which is associated with XLSA/A. Thus, the mtABC7 polypeptide will prove useful in identifying subjects that are carriers for, are at risk for, or have XLSA/A, as described more fully below.

The invention also provides polynucleotides encoding wtABC7 protein. These polynucleotides include DNA, cDNA and RNA sequences which encode wtABC7. It is understood that all polynucleotides encoding wtABC7 are also included herein, so long as they encode a polypeptide with wtABC7 activity. Such polynucleotides include naturally occurring, synthetic, and intentionally manipulated polynucleotides. For example, wtABC7 polynucleotide may be subjected to site-directed mutagenesis. The polynucleotide sequence for wtABC7 also includes antisense sequences, and sequences encoding dominant negative forms of wtABC7. The polynucleotides of the invention include sequences that are degenerate as a result of the genetic code. There are 20 natural amino acids, most of which are specified by more than one codon. Therefore, all degenerate nucleotide sequences are included in the invention so long as the amino acid sequence of ABC7 polypeptide encoded by the nucleotide sequence is functionally unchanged.

Specifically disclosed herein is a polynucleotide sequence containing the wtABC7 gene. An exemplar wtABC7 polynucleotide sequence has the sequence as set forth in SEQ ID NO:1. The term "polynucleotide" or "nucleic acid sequence" refers to a polymeric form of nucleotides. By "isolated polynucleotide" is meant a polynucleotide that is not immediately contiguous with both of the coding sequences with which it is immediately contiguous, (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA.

The invention also provides a polynucleotide encoding the mtABC7 polypeptide. An exemplary mtABC7 polynucleotide sequence is set forth in SEQ ID NO:3. It is understood that any polynucleotide complementary to SEQ ID NO:3 or any fragment thereof are encompassed by the present invention, for example such polynucleotides may include DNA, RNA, mRNA, cDNA and others.

The polynucleotides of the invention encoding wtABC7 and mtABC7 include SEQ ID NO:1, SEQ ID NO:3, dominant negative forms of ABC7, and nucleic acid sequences complementary to SEQ ID NO:1 and SEQ ID NO:3. A complementary sequence may include an antisense nucleotide. When the sequence is RNA, the deoxynucleotides A, G, C, and T of SEQ ID NO:1 and SEQ ID NO:3 are replaced by ribonucleotides A, G, C, and U, respectively. Also included in the invention are fragments of the above-described nucleic acid sequences that are at least 15 bases in length, which is sufficient to permit the fragment to specifically hybridize to polynucleotide that encodes the protein of SEQ ID NO:2 or SEQ ID NO:4 under physiological conditions or a close family member of ABC7. The term "specifically hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions,.e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically. The nucleotide sequence encoding the ABC7 polypeptides of the invention include the disclosed sequences and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Given the extensive conservation of amino acid sequences between species, it would now be routine for one of skill in the art to obtain the mitochondrial specific ATP-binding transporter gene-7 nucleic acid and amino acid sequence from any species,.including those provided herein (i.e., human). For example, it is believed that other primate nucleic acid and amino acid sequences are now readily obtainable using the ABC7 sequences of the invention or fragments thereof as a probe. One of skill in the art can determine the percentage of sequence identity between species by aligning the encoded amino acid sequences, determining the corresponding alignment of the encoding polynucleotides, and then counting the number of residues shared between the sequences being compared at each aligned position (see for example FIG. 1). No penalty is imposed for the presence of insertions or deletions, but insertion or deletions are permitted only where required to accommodate an obviously increased number of amino acid residues in one of the sequences being aligned. Offsetting insertions just to improve sequence alignment are not permitted at either the polypeptide or polynucleotide level. Thus, any insertions in the polynucleotide sequence will have a length which is a multiple of 3. The percentage is given in terms of residues in the test sequence that are identical to residues in the comparison reference sequence.

Percent identity is calculated for oligonucleotides of this length by not allowing gaps in either the oligonucleotide or the polypeptide for purposes of alignment. Throughout this disclosure, whenever at least one of two sequences being compared is a degenerate oligonucleotide comprising an ambiguous residue, the two sequences are identical if at least one of the alternative forms of the degenerate oligonucleotide is identical to the sequence with which it is being compared. As an illustration, AYAAA is 100% identical to ATAAA, since AYAAA is a mixture of ATAAA and ACAAA. Methods to determine the homology and percent identity of sequences are well known in the art. These methods can be performed manually (using mathematical calculations) or with a computer program, such as BLAST (Altschul et al., 1986, Bull. Math. Bio. 48:603–616).

Other ABC7 polypeptides included in the invention are polypeptides having amino acid sequences that are at least 50% identical to the amino acid sequence of a ABC7 polypeptide, such as any of ABC7 polypeptides in SEQ ID NOs:2 and 4. The length of comparison in determining amino acid sequence homology can be, for example, at least 15 amino acids, for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 5.3705; also see Ausubel, et al., supra). Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignmient), ASSET (Aligned Segment Statistical Evaluation Tool), BANTDS, BESTSCOR, BIO-SCAN (Biological Sequence Comparative Analysis Node), BLIMPS (BLocks IMProved Searcher), FASTA, Intervals & Points, BMB, CLUSTAL. V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF.

As known in the art "similarity" between two polypeptides is determined by comparing the amino acid sequence and its conserved amino acid substitutes of one polypeptide to the sequence of a second polypeptide. Similarity in nucleic acid and amino acid sequences may be determined by procedures and algorithms which are well-known in the art. Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W. CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP MBLKN, PIMA (Pattern-Induced Multi-sequence Alignment), SAGA (Sequence Alignment by Genetic Algorithm) and WHAT-IF.

DNA sequences encoding ABC7 can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the ABC7 polynucleotide sequences may be inserted into an expression vector. The term "expression vector" refers to a plasmid, virus or other vehicle known in the art that has been manipulated by insertion or incorporation of the ABC7 genetic sequence. Polynucleotide sequence which encode ABC7 can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present, invention, the polynucleotide encoding an ABC7 may be inserted into an expression vector which contains a promoter sequence which facilitates the efficient transcription of the inserted genetic sequence of the host. The expression vector typically contains, an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding an ABC7 (e.g., wtABC7 or mtABC7) can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which) has been introduced, by means of recombinant DNA techniques, a DNA molecule encoding wtABC7 or mtABC7. Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding an ABC7 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform. eukaryotic cells and express the protein (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

ANTIBODIES

The ABC7 polypeptides of the invention can be used to produce antibodies which are immunoreactive or bind to epitopes of an ABC7 polypeptide (e.g., wtABC7 or mtABC7). Antibodies which consist essentially of pooled monoclonal antibodies with different epitopic specificities, as well as distinct monoclonal antibody preparations are provided.

It is understood that antibodies may be developed to both the wtABC7 and the mtABC7. For example, antibodies to the mtABC7 may prove useful in the identification of an organism that carries a mutant ABC7. The antibodies may be useful in the identification of organism, such as humans, which have XLSA/A or an ABC7 related disease. Additionally, antibodies which are directed to epitopes including amino acid residue 395 may be useful in distinguishing wtABC7 containing 395I from mtABC7 containing 395M.

The preparation of polyclonal antibodies is well-known to those skilled in the art. See, for example, Green et al., "Production of Polyclonal Antisera," in: *Immunochemical Protocols* pages 1–5, Manson, ed., Humana Press 1992; Coligan et al., "Production of Polyclonal Antisera in Rabbits, Rats, Mice and Hamsters," in: *Current Protocols in Immunology*, section 2.4.1, 1992, which are hereby incorporated by reference.

The preparation of monoclonal antibodies likewise is conventional. See, for example, Kohler & Milstein, *Nature* 256:495, 1975; Coligan et al., sections 2.5.1–2.6.7; and Harlow et al., in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)," in: *Methods in Molecular Biology*, Vol. 10, pages 79–104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465, 1991, and Losman et al., *Int. J. Cancer* 46:310, 1990, which are hereby incorporated by reference.

Alternatively, a therapeutically useful anti-ABC7 (including anti-wtABC7 and anti-mtABC7) antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques, for cloning murine immunoglobulin variable domains are described, for example, by Orlandi et al., *Proc. Nat'l Acad. Sci. USA* 86:3833, 1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeven et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

Antibodies of the invention also may be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994, which are hereby incorporated by reference.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., *Arch. Biochem. Biophys*. 89:230, 1960; Porter, *Biochem. J*. 73:119, 1959; Edelman el al., *Methods in Enzymology*, Vol. 1, page 422, Academic Press, 1967; and Coligan el al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$, and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: a Companion to Methods in Enzymology*, Vol. 2, page 97, 1991; Bird el al., *Science* 242:423–426, 1988; Ladner el al., U.S. Pat. No. 4,946,778; Pack et al., *Bio/Technology* 11: 1271–77, 1993; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol 2, page 106,1991.

Antibodies which bind to an ABC7 polypeptide (including wtABC7 and mtABC7) of the invention can be prepared using an intact polypeptide or fragments containing small peptides of interest as the immunizing antigen. For example, a fragment containing the mutant polypeptide sequence at about amino acid residue 395 of SEQ ID NO:4 may be used to identify mutant organisms. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

METHOD FOR IDENTIFYING COMPOUNDS WHICH AFFECT ABC7

The invention also provides a method for identifying a compound or agent which can modulate ABC7 activity. This method may prove useful in identifying compounds which may alter the disease state associated with the mtABC7. The method includes incubating a compound or agent and a sample containing ABC7 polynucleotide or polypeptide under conditions sufficient to allow the components to interact, and measuring the effect of the compound on the expression or activity of ABC7 polynucleotide or polypeptide, respectively. In one embodiment, the sample is a cell expressing wtABC7 or mtABC7 polypeptide or polynucleotide. The activity of ABC7 in the sample can then be compared to the ABC7 activity of a control sample not incubated with the compound. For example, activity of ABC7 can be identified by measuring a second messenger response or signaling event.

A "second messenger response" or "signaling event" means the generation of a biochemical or physiological response as a result of contacting the compound with a sample containing an ABC7 polypeptide or polynucleotide. In general, a signaling event results in the change of a molecular characteristic or parameter of the cell. Non-limiting examples include ion fluxes (e.g., an iron flux), enzyme activation (e.g., a ferrochelatase activity), changes in cyclic nucleotides (e.g., cAMP, cADP, cGMP, cGDP, etc.), among others. A specific, example is the generation of a $Fe^{2+}$ flux following the interaction of a compound with ABC7. For example, the increase or decrease in iron concentrations in the mitochondria of a treated subject, sample, or mitochondrial preparation.

The effect of a compound or agent on ABC7 can be measured by assessing the expression of ABC7 by methods well known in the art (e.g., Northern blots). Alternatively, the effect of the compound on the activity of ABC7 can be assessed by measuring the signaling event by any means known to one of skill in the art. For example, in order to determine the effect of the compound on the activity of ABC7, iron transport can be measured. For example, sideroblastic anemias are disorders, characterized by hypochromic microcytic erythrocytes and iron accumulation in the mitochondria of bone marrow erythrocyte precursors. The disorder can be both acquired or inherited, and the mode of transmission may be mitochondrial, autosomal or X-linked. In addition to the hypochromic microcytic anemia seen in subjects having these disorders, the affected males as well as carriers have elevated levels of free erythrocyte protoporphyrins (FEP). Elevations of FEP are indicative of a defect in ferrochelatase activity, which catalyzes the insertion of iron into the protoporphyrin ring in the final step of heme biosynthesis.

Alternatively, a "physiological indicator" can be used to measure the signaling event. A "physiological indicator" is any compound in which a measurable property changes in a response to a physical parameter of the cell. Cell signaling events that occur in vivo can be of very short duration. The physiological indicators can allow measurement of the physiological parameter over the same time period that the event actually occurs, or after the event occurs (over a longer time period). One nonlimiting example of a measurable property is a change in fluorescence of an physiological indicator in response to an iron flux.

Fluorescence is one spectral property of which can be used as the means of detecting a physiological parameter of a cell. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between a cell contacted with a compound of interest as compared to a control cell suffices to identify a compound which can modulate ABC7 activity. A measurable difference can be determined by determining the amount of any quantitative fluorescent property, e.g., the amount of fluorescence at a particular wavelength, or the integral of fluorescence over the emission spectrum. Optimally, the physiological indicator is selected to have fluorescent properties that are easily distinguishable.

The compounds which affect ABC7 include peptides, polypeptides, polynucleotides, chemical compounds and biological agents.

A compound can affect ABC7 by either stimulating or inhibiting ABC7. For example, a compound "inhibits" ABC7 if the ability to transport iron is decreased, similarly a compound "stimulates" ABC7 if the ability to transport iron is increased.

The sample can be any sample of interest. The sample may be a cell sample, fractionated cell samples (such as a sample containing mitochondria or organelles of interest) or a membrane sample prepared from a cell sample. Suitable cells include any host cells containing a recombinant ABC7 vector of the invention. Alternatively, cell lines expressing ABC7 polypeptide can be used.

The binding affinities of compounds which affect an ABC7 can also be determined in either cells, organelles or a membrane preparation expressing an ABC7. In these assays, a labeled ligand is employed. A number of labels have been indicated previously (e.g., radiolabels, fluorescence labels, among others) to be of use. The candidate compound is added in an appropriate buffered medium. After an incubation to ensure that binding has occurred, the surface may be washed free of any nonspecifically bound components of the assay medium, particularly any nonspecifically bound labeled ligand, and any label bound to the surface determined. The label may be quantitatively measured. By using standards, the relative binding affinity of a candidate compound can be determined.

The antibodies, polypeptides, and polynucleotides of the invention can be used to detect or treat a ABC7-associated disorder or an ABC7-related disorder. The term "ABC7-associated disorder" denotes disorders in ABC7 function itself. These disorders may be understood to be include defects in other molecules known to participate in ABC7 activity.

Essentially, any disorder which is etiologically linked, as either an ABC7-associated or ABC7-related disorder, to increased expression of ABC7 could be considered susceptible to treatment with a ABC7 suppressing reagent, and any disorder which is etiologically linked, as either an ABC7-associated or ABC7-related disorder, to decreased expression of ABC7 could be considered susceptible to treatment with ABC7 activating reagents, including treatments with polynucleotides encoding ABC7 or the ABC7 polypeptide itself.

For purposes of the invention, an antibody or hucleic acid probe specific for ABC7, may be used to detect ABC7 polypeptide (using antibody) or polynucleotide (using nucleic acid probe) in subject samples such as biological fluids, cells, fractionated cells (e.g., organelle preparations), tissues, or nucleic acid. Any specimen containing a detectable amount of antigen or polynucleotide can be used. Examples of biological fluids of use with the invention are blood, serum, plasma, urine, mucous, and saliva. Tissue or cell samples can also be used with the subject invention. The samples can be obtained by many methods such as cellular aspiration, or by surgical removal of a biopsy sample.

The invention provides a method for detecting an ABC7, which comprises contacting an ABC7 antibody or nucleic acid probe with a cell suspected of expressing the mtABC7 and detecting binding to the antibody or nucleic acid probe. The antibody reactive with a mtABC7 or the nucleic acid probe is preferably labeled with a compound which allows detection of binding to mtABC7. The level of the mtABC7 in the subject cell can be compared with the level in a cell not affected by the disease process. The cell not affected by the disease process can be taken from the same subject, or can be from a control subject not affected by the disease process, or can be from a cell line. Preferably the subject is human. One can distinguish the alleles of ABC7 that are expressed, e.g., different CAG repeat lengths, point mutations.

When the cell component is nucleic acid, it may be necessary to amplify the nucleic acid prior to binding with the ABC7 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Those of skill in the art will know, or can readily discern, an appropriate immunoassay format without undue experimentation.

The antibodies of the invention can be bound to many different carriers, both soluble and insoluble, and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in efficient quantity to enable detection of the site having the antigen comprising a polypeptide of the invention for which the monoclonal antibodies are specific.

The monoclonal antibodies or polynucleotides of the invention can be used in vitro and in vivo to monitor the course of amelioration of a ABC7-associated disease in a subject. Thus, for example, by measuring the increase or decrease in the number of cells expressing antigen comprising a polypeptide of the invention or changes in the concentration of such antigen present on cells or in various body fluids, it would be possible to determine whether a particular therapeutic regimen aimed at ameliorating the ABC7-associated disease is effective. The term "ameliorate" denotes a lessening of the detrimental effect of the ABC7-associated disease in the subject receiving therapy.

THERAPEUTIC TECHNIQUES

The present invention identifies a polynucleotide sequence that can be expressed in an altered manner as compared to expression in a normal cell, or that expresses an altered gene product. Therefore it is possible to design appropriate therapeutic or diagnostic techniques directed to this sequence. The antibodies and polynucleotides of the invention can be used to detect or to treat an ABC7-associated disorder.

Detection of elevated levels of ABC7 expression is accomplished by hybridization of nucleic acids isolated from a cell of interest with an ABC7 polynucleotide of the invention. Analysis, such as Northern Blot analysis, are utilized to quantitate expression of the ABC7. Other standard nucleic acid detection techniques will be known to those of skill in the art.

Treatment can include modulation of ABC7 gene expression and/or ABC7 activity by administration of a therapeutically effective amount of a reagent that modulates the ABC7 expression or activity. The term "modulate" envisions the suppression of expression of ABC7 when it is overexpressed, or augmentation of the expression of ABC7 when it is underexpressed. Where a disorder is associated with the decreased expression of wtABC7, nucleic acid sequences that encode wtABC7 can be used. Where a disorder is associated with the increased expression of ABC7, nucleic acid sequences that interfere with the expression of ABC7 can be used. This approach utilizes, for example, antisense nucleic acid, ribozymes, or triplex agents to block transcription or translation of ABC7 mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American* 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target ABC7-producing cell. The use of antisense methods to inhibit the in vitro translation of genes is well known in the art (Marcus-Sakura, *Anal. Biochem.* 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, el al., *Antisense Res. and Dev.* 1(3):227, 1991; Helene. C., *Anticancer Drug Design* 6(6):569), 1991.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.* 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of disorders which are associated with ABC7 protein. Such therapy would achieve its therapeutic effect by introduction of a therapeutic polynucleotide into cells having the disorder. The "therapeutic polynucleotide" may be a polynucleotide sequence encoding wtABC7, or antisense polynucleotide specific for mtABC7, designed to treat an ABC7-associated disorder. Delivery of the therapeutic polynucleotide can be achieved using a recombinant expression vector such as a chimeric virus or a colloidal dispersion system. Especially preferred for therapeutic delivery of antisense sequences, or ABC7 polynucleotides, is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting an ABC7 sequence of interest into the viral vector, along with another gene which encodes the ligand for a receptor on a specific target cell, for example, the vector is now target specific. Retroviral vectors can be made target specific by attaching, for example, a sugar a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing an ABC7 polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulated a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. *Biotechniques* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the target delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Thus the identification of ABC7 provides a useful tool for diagnosis, prognosis and therapeutic strategies associated with expression of ABC7.

KITS

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be an antibody or nucleic acid sequence specific for ABC7, or specific fragments thereof. For example, oligonucleotide probes of the present invention can be included in a kit and used for examining the presence of mtABC7 in a sample, as well as the quantitative (relative) degree of binding of the probe for determining the occurrence of specific strongly binding (hybridizing) sequences, thus indicating the likelihood for an subject having or predisposed to a disorder associated with ABC7.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the ABC7 target sequence, this can be accomplished using oligonucleotide(s) that are primers for amplification. These oligonucleotide primers are based upon identification of the flanking regions contiguous with the target nucleotide sequence.

The kit may also contain a container containing antibodies which bind to ABC7, or specific fragments thereof Such antibodies can be used to distinguish the presence of mtABC7 or the level of expression of ABC7 in a specimen. Where the kit utilizes antibodies to detect mtABC7, these antibodies may be directly labeled. The kit may also contain a container containing a reporter means such as avidin or streptavidin, bound to a reporter molecule such as an enzymatic, fluorescent, or radionucleotide label to identify the directly labeled antibody. Alternatively, the kit can utilize antibodies that bind ABC7 that are unlabeled. The kit may then also contain a container containing a second antibody which binds to the antibody specific for ABC7. The second antibody can be directly labeled. The kit may also contain a container containing a reporter means, such as avidin or streptavidin, bound to a reporter molecule such as an enzymatic, fluorescent, or radionucleotide label to identify the directly labeled second antibody.

TRANSGENIC ANIMALS

In another embodiment, the present invention relates to transgenic animals having cells that express ABC7. Such transgenic animals represent a model system for the study of ABC7 related disorders, such as XLSA/A, and for the study of ABC7 based therapeutics.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

It is highly preferred that the transgenic animals of the present invention be produced by introducing into single cell embryos DNA encoding either wtABC7 or mtABC7, in a manner such that the polynucleotides are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo.

In a most preferred method the appropriate DNAs are coinjected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et.al., *Manipulating the Mouse Embryo*, Cold Spring Harbor Press, 1986; Krimpenfort et al., *Bio/Technology* 9:86, 1991; Palmiter et al, *Cell* 41:343, 1985; Kraemer et al, *Genetic Manipulation of the Early Mammalian Embryo*, Cold Spring Harbor Laboratory Press, 1985; Hammer et al., *Nature*, 315:680, 1985; Purcel et al., *Science*, 244:1281, 1986; Wagner et al., U.S. Pat. No. 5,175,385; Krimpenfort et al., U.S. Pat. No. 5,175,384, the respective contents of which are incorporated by reference.

The cDNA that encodes ABC7 can be fused in proper reading frame under the transcriptional and translational control of a vector to produce a genetic construct that is then amplified, for example, by preparation in a bacterial vector, according to conventional methods. See, for example, the standard work: Sambrook et al., *Molecular Cloning: a Laboratory Manual*, Cold Spring Harbor Press, 1989, the contents of which are incorporated by reference. The amplified construct is thereafter excised from the vector and purified for use in producing transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered nonfunctional by homologous recombination. As used herein, the term "transgenic" includes any transgenic technology familiar to those in the art which can produce an organism carrying an introduced transgene or one in which an endogenous gene has been rendered non-functional or knocked out.

The transgene to be used in the practice of the subject invention is a DNA sequence comprising a modified ABC7 coding sequence. In a preferred embodiment, the endogenous ABC7 gene is disrupted by homologous targeting in embryonic stem cells. For example, the entire murine ABC7 gene may be deleted. Optionally, the ABC7 disruption or deletion may be accompanied by insertion of or replacement with other DNA sequences, such as a non-functional ABC7 sequence such as mtABC7. In other embodiments, the transgene comprises DNA antisense to the coding sequence for ABC7. In another embodiment, the transgene comprises DNA encoding an antibody or receptor peptide sequence which is able to bind to ABC7. Where appropriate, DNA sequences that encode proteins having ABC7 activity but differ in nucleic acid sequence due to the degeneracy of the genetic code may also be used herein, as may truncated forms, allelic variants and interspecies homologues.

DIAGNOSTIC TECHNIQUES

Detection of the ABC7 Allele

In addition, the invention may be used to identify or treat individuals who are "at risk" of developing a ABC7-associated disorder or transmitting an allele carrying a mutant ABC7 to their offspring. These individuals may be identified by a method of the invention for detecting the presence or absence of ABC7 or by any other diagnostic means, and/or may be treated by a method of the invention.

"Homozygous" is defined as two of the same alleles for a given gene. According to the present invention, the ABC7 gene (wt or mt), like most eukaryotic genes, at a frequency of two copies per genome. If both copies are genetically the same, in regard to a polynucleotide encoding either methionine or isoleucine at position 395, the individual is homozygous, i.e. either wt/wt or mt/mt.

"Heterozygous" is defined as two different alleles being present in the genome for a given gene. According to the present invention, if one copy each of wt and mt ABC7 are present in the genome, the individual is heterozygous.

The term "allelic profile" means a determination of the composition of an individuals genome in regard to the presence or absence, and the copy number of the ABC7 allele.

Determination of the likelihood that an individual may be subject to an ABC7-associated disease and or is a carrier for such a mutant gene provides a way to make rational choices of treatment. The diagnostic methods enabled by the present invention can be generally regarded as of two types. Diagnostics using nucleic acid primers for amplification of a nucleic acid or hybridization probes, and diagnostics employing antibodies directed to the mtABC7 or the product of the mtABC7 gene. The amplification of a nucleic acid can be accomplished by one of a number of methods known to one skilled in the art. By way of example, amplification by PCR is described below. Alternatively, wt-antibodies can be used to pull out the protein for further analysis OF the amino acid sequence.

PCR Based Diagnostics

The allelic profile of a patient can be determined by employment of PCR technology. The target nucleic acid to be amplified by PCR would be either the mtABC7 RNA (through the production of cDNA) or, in a preferred embodiment, the mtABC7 gene. Primers are designed in order to amplify the sequence including amino acid 395 of the mtABC7 sequence. By judiciously choosing primers and reaction conditions, one can obtain a fragment which is indicative of the presence or absence of the mutation. One skilled in the art would recognize variations on this motif. For example, the PCR reaction may contain labeled oligonucleotides to facilitate subsequent detection of the PCR product. The label can be, for example, radiolabeled nucleotides, or biotin incorporating nucleotides. According to such a diagnostic procedure employing PCR, either wt or mt homozygote will produce an amplified product having an expected sequence.

Hybridization-Probe Based Diagnostics

An oligonucleotide can be designed which under known experimental conditions can form a stable hybrid with a target nucleic acid sequence. Typically, such experimental conditions include incubation in high salt at 65° C., or incubation of 42° C. in the presence of formamide, although one skilled in the art can readily define other experimental conditions to allow stable hybrid formation. Consideration as to the optimum size of the hybridizing oligonucleotide under a set of experimental conditions are well known to one skilled in the art (see Maniatis et al., supra).

Typically, oligonucleotides would be between 12 and 25 nucleotides in length, though use of shorter and longer oligonucleotides is possible. In a typical hybridization probe based diagnostic test, the targeted nucleic acid is blotted on a membrane. Alternatively, the target nucleic acid is digested by restriction endonucleases, electrophoresed on a gel, and then blotted onto a membrane. The hybridizing probe is labeled (typically by incorporating radionucleotides).

Diagnostics Based on the Use of Antibodies

Antibodies and monoclonal antibodies directed to wtABC7 or mtABC7 polypeptides can be obtained by methods disclosed above. In a preferred embodiment, blood serum samples derived from the patient is treated by standard methods to disrupt the cells, which can then be followed by a limited purification of the sample. The product is then analyzed by ELISA. Alternatively the crude preparation is run on a polyacrylamide gel blotted onto membranes, and assayed by Western Blotting. At this point, separate use of the anti-wtABC7 antibody and the anti-mtABC7 antibody can reveal the homozygous or the heterozygous condition. Such methods of partial purification of an extract and ELISA and Western blotting are well-known to one of skill in the art (see Maniatis, supra).

The invention also provides a method of determining the prognosis of a subject by detecting the amount of mutant ABC7. The amount of ABC7 present in the subject may be determined by any number of means as discussed above. For example, polynucleotide levels may be determined by Southern, Northern, PCR or other techniques well known to those skilled in the art. Polypeptide levels may be determined by ELISA methods, Western Blots or other techniques well known to those skilled in the art. These levels may then be compared to a normal or standard level of ABC7. Elevated amounts of mtABC7 are indicative of the severity of an ABC7 associated disease. In addition, levels of mtABC7 can be determined before and after treatment with an agent or by gene therapy techniques. The levels of mtABC7 present will be indicative of the success of the treatment or therapy.

In addition, sideroblastic anemias are disorders, characterized by hypochromic microcytic erythrocytes and iron accumulation in the mitochondria of bone marrow erythrocyte precursors. The disorder can be both acquired or inherited, and the mode of transmission may be mitochondrial, autosomal or X-linked. In addition to the hypochromic microcytic anemia seen in subjects having these disorders, the affected males as well as carriers have elevated levels of free erythrocyte protoporphyrins (FEP). Elevations of FEP ,are indicative of a defect in ferrochelatase activity, which catalyzes the insertion of iron into the protoporphyrin ring in the final step of heme biosynthesis. This is likely the result of iron accumulation in the mitochondria that is unavailable for utilization by ferrochelatase in these individuals. In the alternative, the accumulated iron may lead to direct inactivation of ferrochelatase. This enzyme contains an iron-sulfur center which could be destroyed by superoxide in association with the observed decrease in aconitase activity. The elevation of FEP seen in subjects having a mutation of ABC7 serves as a useful clinical marker to distinguish them from patients with other forms of sideroblastic anemia, which are usually characterized by normal or decreased FEP.

All references cited herein are hereby incorporated by reference in their entirety.

The present invention is not to be limited in scope by the specific examples provided for below, which are intended as single illustrations of individual aspects of the invention and functionally equivalent methods and components are within the scope of the invention.

EXAMPLES

Figure 3:
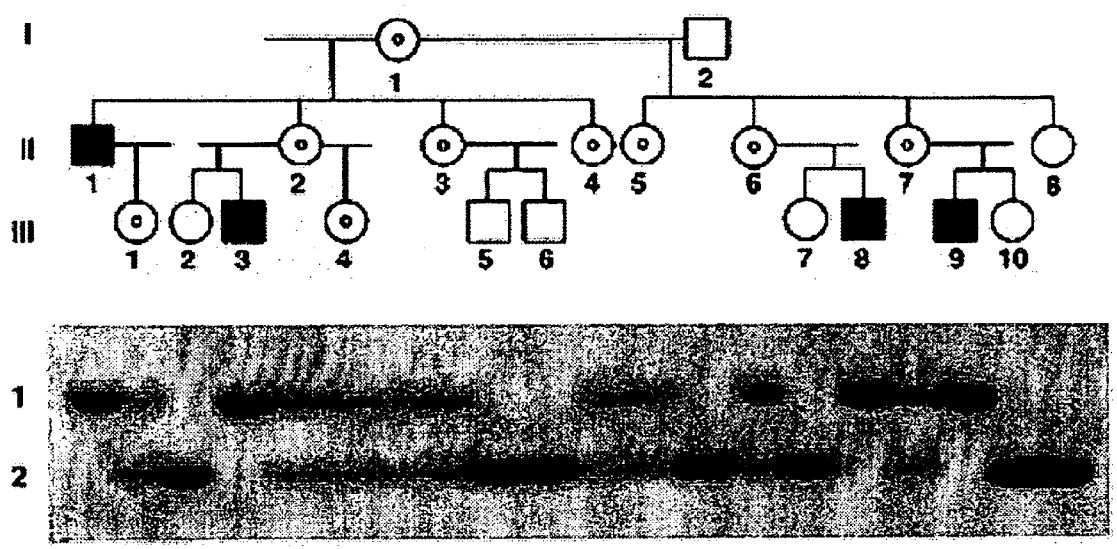
FIG. 3 shows segregation of SSCP variant of the I395 mutation in the ABC7 gene in kindred with XLSA/A. Sequence analysis of SSCP bands (shown below the pedigree) revealed the existence of wild type sequence (band 2) and mutant sequence (band 1). DNA sequencing revealed a T1200G (I395M) substitution in the band 2. Female carriers are heterozygous for the T1200G (I395M) substitution (reveal both bands 1 and 2), while the affected male offspring (individuals II-1; III-3, III-8 and III-9) harbor the mutant ABC7 allele only. Haplotype analysis previously demonstrated homozygosity at the XLSA/A locus in all affected individuals.

XLSA/A Kindred and Samples. Subjects gave informed consent and were evaluated and sampled under protocols approved by the University of Washington Institutional Review Board. The members of the family are identified by their pedigree positions as shown in FIG. 3. Individuals II-1, III-3, III-8 and III-9 are affected males. Individuals I-2, II-2, II-5, II-6, II-7 and III-1 are obligate heterozygotes. A sample was not obtained from the affected son of II-5 (not shown). Although neither II-3 nor I-4 have affected children and their free erythrocyte proporphyrin levels were normal, marrow examination of both revealed ringed sideroblasts, strongly suggesting that they are also carriers of XLSA/A. II-8 has one unaffected son (not shown) and was shown to have normal free erythrocyte proporphyrin levels.

Some members of the family described have isoleucine substituted for methionine at amino acid position 395 in the ABC7 proteins, located near the carboxy terminus of the predicted fifth membrane spanning α-helix (FIG. 1). In all closely related ABC transporters, including Hmt1p, Atm1p, and two other superfamily members from *S. Cerevisiae*, Md11p and Md12p, this residue is either an isoleucine or valine, indicating a high degree of evolutionary conservation (FIG. 1). The functional consequences of the Ile to Met substitution, which are both hydrophobic residues, are apparently relatively minor, given the non-progressive nature of the ataxia and relatively mild anemia seen in this kindred.

In addition to the hypochromic microcytic anemia seen in this family, the affected males as well as several obligate carriers have elevated levels of free erythrocyte protoporphyrin (FEP). Elevations of FEP are indicative of a defect in ferechelatase activity, which catalyzes the insertion of $Fe^{2+}$ into the protoporphyrin ring in the final step of heme biosynthesis. There are at least two possible explanations of this finding; the first is that the iron accumulated in the mitochondria of these patients is unavailable for utilization by ferrochelatase. Alternatively, the accumulated iron may lead to direct inactivation of ferrochelatase. This enzyme contains an iron-sulfur center which could be destroyed by superoxide as described above in association with the observed decrease in aconitase activity. The elevation of FEP seen in patients with a mutation of ABC7 should serve as a useful clinical marker to distinguish them from patients with other forms of Sideroblastic anemia, which are usually characterized by normal or decreased FEP.

cDNA Cloning. In the original linkage study, the XLSA/A locus was mapped close to the phosphoglycerate kinase (PGK1) gene on Xq13, in a region bounded by AR and DXYS1 (Raskind el al., 1991). Previously, we had mapped the ABC7 gene to the same band of the human X chromosome by in situ hybridization (Savary et al., 1997). To refine the localization of ABC7, we mapped the gene on GeneBridge4 radiation hybrid panel, confirming the close proximity of ABC7 and PGK 1, between markers DX983–DXS995 on Xq13.

cDNA clones containing ABC7 sequences were obtained from Research Genetics and Genome Systems and sequenced fully. Primers were designed from the compiled contig of the ABC7 cDNA sequence from 5' and 3' regions of the gene, and used to amplify the full-length ABC7 gene sequences by PCR with human placenta QUICK-Clone cDNA (Clontech) as a template. Amplification was performed with AmpliTaq Gold polymerase in a 25 ul volume in 1X PCR buffer supplied by the manufacturer (Perkin Elmer). Samples were heated to 95° C. for 10 min and amplified for 35–40 cycles of 96° C., 20 sec; 58° C., 30 sec; 72° C., products were analyzed on 1–1.5% agarose gels and in some cases digested with an appropriate restriction enzyme to verify their sequence. PCR products were cloned into pGEM-T vector (Promega) and verified by direct sequencing using forward primer 5'-GCGATGCATTCTTGGCGCTG-3' (SEQ ID NO:3) and reverse primer 5'-TGCTTCAGTGCAAATATG TAGTC-3' (SEQ ID NO:5). The sequence of the ABC7 cDNA has been deposited with GenBank under accession #AF328787.

The human ABC7 gene was initially characterized as a half-transporter and a member of the MDR/TAP subfamily (EST140535; Alikmets et al., 1996). Subsequently, the gene was precisely localized to Xq13 and the mouse ortholog, abc7, characterized. (Savary et al, 1997). To isolate the full-length human ABC7 gene the 5' RACE was performed, together with the search of the expressed sequence tags database (dbEST; Boguski et al., 1993). As established earlier, both human and mouse ABC7 proteins were the most closely related to two yeast ABC transporters, *S. Cerevisiae* Atm1 p and *S. Pome* Hmt1p (Savary et al., 1997). The striking conservation of these proteins—more than 50% identity over 200 aa within the ATP-binding domains—led us to the conclusion that ABC7 transporters in mouse and human are indeed orthologs of the yeast proteins (FIG. 1). Sequence identity is almost as high (near 50%) in the transmembrane segments as well, suggesting that these proteins could transport similar substrates. Moreover, the phylogenetic analysis revealed that the human ABC7 protein is more closely related to two yeast transporters than to the other members of the human MDR/TAP subfamily of the ABC superfamily.

The open reading frame (ORF) of the human ABC7 gene contains 2240 base pairs (747 amino acids) and encodes for a half-transporter, consisting of six membrane spanning hydrophobic segments and an ATP-binding domain (FIG. 1). The transmembrane domains, predicted by a hydropathy plot, aligned perfectly with the corresponding segments of the yeast Atm1p transporter (Leighton and Schatz, 1995; GenBank accession #1352002). The highly conserved ATP-binding domain contained characteristic Walker A and B motifs and the Signature C motif (FIG. 1). As ABC transporters are composed of two ATP and two transmembrane domains, the ABC7 protein is predicted to form a homodimer or heterodimer with another half-molecule (Hyde et a., 1990).

As opposed to the yeast Atm1p (Leighton and Schatz, 1995), the mitochondrial inner membrane localization of the human ABC7 protein has not been directly demonstrated. However, the N-terminal protein sequence of ABC7 reveals a characteristic mitochondrial targeting signal (Schatz, 1987), consisting of a string of basic, positively charged residues (FIG. 1). The protein was localized to mitochondrial inner membrane also by the PSORT (Prediction of Protein Sorting Signals and Localization Sites in Amino Acid Sequences; http://psort.nibb.ac.jp; Nakai and Kanehisa, 1992) program, that utilizes both N-terminal and internal signal sequences, with a certainty) factor of 0.857. Given the extraordinarily high protein sequence homology between Atm1p and ABC7, and taking into account the presence of signal sequences, it can be predicted that the ABC7 protein is localized to the mitochondrial inner membrane.

Sequencing and Sequence Analysis. Primers for the cDNA sequences of the ABC7 were designed with the PRIMER program. Both ABC7 cDNA clones and genomic clones became templates for sequencing. Sequencing was performed with the Taq Dideoxy Terminator Cycle Sequencing kit (Applied Biosystems), according to the manufacturer's instructions. Sequencing reactions were resolved on an ABI 373A automated sequencer. Searches of the dbEST database were performed with BLAST on the NCBI file service. Amino acid alignments were generated with PILEUP. Sequences were analyzed with programs of the Genetics Computer Group package on a VAX computer.

Mutation Detection. Mutation detection was performed by direct sequencing of PCR products, obtained by RT-PCR (GeneAmp Kit, Perkin Elmer) using mRNA as a template. Segregation analysis and screening of controls were performed by SSCP (Orita et al., 1989) analysis under optimized conditions (Glayac and Dean, 1993). Genomic DNA samples (50 ng) were amplified with AmpliTaq Gold polymerase in 1×PCR buffer supplied by the manufacturer (Perkin Elmer) containing [α-32P] dCTP. Samples were heated to 95° C. for 10 min and amplified for 35–40 cycles of 96° C., 20 sec; 58° C., 30 sec; 72 ° C., 30 sec. Products were diluted in 1:3 stop solution, denatured at 95° C. for 5 min, chilled in ice for 5 min, and loaded on gels. Gel formulations included 6% acrylamide:Bis (2.6% cross-linking), 10% glycerol at room temperature, 12 W; and 10% acrylamide:Bis (1.5% cross-linking), at 4° C., 70 W. Gels were run for 2–16 hours (300 Vh/100 bp), dried and exposed to X-ray film for 2–12 hours.

Mutational analysis of the ABC7 gene was pursued in the previously ascertained XLSA/A kindred (Pagan et al., 1985). Purified mRNA and DNA was isolated for all available family members from previously established B-lymphoblastoid cell lines (Raskind et al., 1984). RT-PCR and direct sequencing methods were utilized on mRNA of 4 out of 5 affected individuals and of the obligate carrier grandmother. Only one sequence variant was detected (T1200G (see FIGS. 1B and 1C) that changes the amino acid sequence, from Ile to Met, at position 395 (I395M), within the predicted fifth transmembrane domain of the ABC7 gene (TM5; FIG. 1). Specific PCR primers were designed for this variant and the DNA of all available family members was screened by the single strand conformation polymorphism (SSCP) technique (Orita et al., 1989). The I395M substitution was found to segregate in the family and was detected in all affected individuals and, in heterozygous state, in female carriers (FIG. 3). In addition to obligate carriers, the I395M allele was found also to be present in individuals III-4, II-3 and II-4. The only other sequence variant detected was the in-frame addition of one amino acid (Gln) at position 50 in the protein sequence in all individuals. This variant occurs in the region of the ABC7 protein that is not conserved and even not present in Atm1p (FIG. 1). Both mRNA variants (with and without the CAG codon) were detected in all cell lines, suggesting that it may be due to differential splice site utilization.

Analysis of the I395M Variant in the Yeast ATM1 gene. To evaluate the functional consequences of the observed I395M substitution in the ABC7 protein, the corresponding mutation was made in the yeast ATM1 gene, resulting in a V365M substitution. The ATM1 gene with the V365M mutation was subsequently tested for its ability to complement an ATM1 gene deletion. Disruption of the ATM1 gene results in a 20 fold decrease in catalase activity and increased sensitivity to oxidative stress. Because of the ability of copper to react with molecular oxygen and form free radicals a differential sensitivity to increased copper can be used to distinguish between wild type and mutated atm1 strains. Transfection of a mutant atm1 strain with the wild type ATM1 gene on a centromeric plasmid results in normal growth in the presence of 1.0 mM CuCl$_2$, a concentration that is lethal of the mutant atm1 strain. A plasmid borne copy of the ATM1 gene with the V365M mutation was unable to complement a mutant atm1 strain under these condition, but did allow growth at 0.4 mM CuCl$_2$, indicating a partial loss of function secondary to this mutation. To test the ability of the human ABC7 protein to complement a mutant atm1 strain the ABC7 cDNA was cloned into a yeast expression vector adjacent to the ADH1 promoter. This plasmid was unable to rescue the mutant atm1 strain under any of the conditions tested. Expression of the ATM1 gene using the ADH1 promoter resulted in complete rescue of the mutant atm1 strain. 0.4 mM CuCl$_2$, indicating a partial loss of function secondary to this mutation. To test the ability of the human ABC7 protein to complement a mutant atm1 strain the ABC7 cDNA was cloned into a y)east expression vector adjacent to the ADH1 promoter. This plasmid was unable to rescue the mutant atm1 strain under any of the conditions tested (FIG. 4). Expression of the ATM1 gene using the ADH1 promoter resulted in complete rescue of the mutant atm1 strain.

The inability of ABC7 to complement an ATM1 deletion could be due either to an inability to function as a homodimer, or to form a functional heterodimer with the yeast dimerization partner for Atm1p. Based on studies of the membrane spanning helixes of another ABC transporter, the cystic fibrosis transmembrane regulator, isoleucine 395 is predicted to be within the lipid bilayer, and not exposed to within the channel. Therefore, the effect of this mutation is predicted to be on assembly of the membrane spanning helixes and/or dimerization, and not on substrate recognition. The modes effect of the V365M mutation on the function of Atm1p may be due to an effect on the interaction with the dimerization partner used by each of the molecules. Incidentally, another half-transporter that maps to 2q35 (EST45597; Allikmets et al., 1996) is structurally very closely related to ABC7. Moreover, the expression patterns of ABC7 and EST45597 were almost identical in all human tissues examined, as judged by the Northern blots.

Based upon both the clinical phenotype of human patients, and the effect of the orthologous mutation on the function of the yeast protein, it appears that the I395M mutation results in a partial loss of function. However, it is expected that the more severe mutation or a complete inactivation of the ABC7 protein would have a more caustic phenotype. A number of disorders with similar or more severe disease manifestations have been mapped by linkage analysis to the same chromosomal region. As an example, Wieacker-Wolff syndrome has been mapped to Xq13-q21 (Kloos et al., 1997). In addition, several reports describe acquired forms of sideroblastic anemia associated with cytogenetic changes in the region of Xq13. It is possible that some of these disorders may be associated with a loss of activity of ABC7. The observation that some patients who present initially with an acquired sideroblastic anemia progress onto myelodysplasia and leukemia may indicate that the accumulation of excess mitochondrial iron is mutagenic.

Northern Hybridization. After demonstrating by both genetic and biochemical analysis that a mutation in the ABC7 gene results in XLSA/A, a correlation of the disease symptoms with the pattern of gene expression was performed. DNA fragments used as probes were purified on a 1% low-melting temperature agarose gel. DNA was labeled directly in agarose with the Random Primed DNA Labeling Kit (Boehringer Mannheim) and hybridized to multiple tissue Northern (MTN) blot (Clontech), according to the manufacturers's instructions. Each blot contains 2 ug of poly A+RNA from various human tissues.

Northern blot analysis revealed that the ABC7 mRNA is present, at various levels, in every human tissue examined (FIG. 2). Significantly higher expression was detected in heart, muscle and pancreas, in tissues with a high rate of metabolism and rich in mitochondria. This observation is consistent with the hypothesis that the human ABC protein, similar to its yeast ortholog Atm1p, is an essential component of mitochondria.

The headings of the various sections and subsections are provided for the reader's convenience and are not to limit the scope of the present invention. A number of embodiments of the present invention have been described. Nevertheless, it will be understood that various modifications may be made without departing from the spirit and scope of the invention. Accordingly, other embodiments are within the scope of the following claims.

What is claimed is:

1. An isolated polynucleotide encoding a polypeptide with the amino acid sequence of SEQ ID NO: 2 or SEQ ID NO: 4.

2. An isolated polynucleotide having a nucleotide sequence consisting essentially of:
   a) SEQ ID NO: 1;
   b) SEQ ID NO: 1, wherein T is U;
   c) nucleic acid sequences complementary to a) or b);
   d) residues 519–1059 of SEQ ID NO: 1;
   e) residues 519–1059 of SEQ ID NO: 1, wherein T is U; or
   f) nucleic acid sequences complementary to d) or e).

3. An isolated polynucleotide having a nucleotide sequence consisting essentially of:
   a) SEQ ID NO: 3;
   b) SEQ ID NO: 3, wherein T is U; or
   c) nucleic acid sequences complementary to a) or b).

4. A vector containing the polynucleotide of claim 1.

5. The vector of claim 4, wherein the vector is a viral vector.

6. The vector of claim 4, wherein the vector is an expression vector.

7. The vector of claim 4, wherein the vector is a plasmid.

8. A host cell containing the vector of claim 4.

9. The host cell of claim 8, cultured under conditions which allow expression of the polynucleotide.

10. A method for producing an ABC7 polypeptide, comprising:
    a) growing a recombinant host cell containing a polynucleotide encoding a polypeptide with the amino acid sequence of SEQ ID NO: 2 or SEQ ID NO: 4 under conditions which allow expression and secretion of the polypeptide; and
    b) isolating the polypeptide.

11. A kit useful for the detection of an ATP-binding transporter-7 (ABC7) polynucleotide comprising carrier means containing therein one or more containers wherein a first container contains a nucleic acid probe comprising at least residues 519–1059 of SEQ ID NO:1; residues 519–1059 of SEQ ID NO: 1, wherein T is U; a nucleic acid sequence complementary to residues 519–1059 of SEQ ID NO: 1; or a nucleic acid sequence complementary to residues 519–1059 of SEQ ID NO: 1, wherein T is U; wherein the nucleic acid probe specifically hybridizes to a polynucleotide having a sequence as set forth in SEQ ID NO: 1 or 3 under conditions at least as stringent as at about room temperature in 2×SSC and 1% SDS with a subsequent wash step at about room temperature in 0.2×SSC and 0.1% SDS.

12. The kit of claim 11, wherein the probe is detectably labeled.

13. The kit of claim 12, wherein the label is selected from the group consisting of radioisotope, a bioluminescent compound, a chemiluminescent compound, a fluorescent compound, a metal chelate, and an enzyme.

14. A kit useful for the detection of an ATP-binding transporter-7 (ABC7) polynucleotide comprising carrier means containing therein two or more containers comprising:
- a) a first container containing a first nucleic acid probe comprising a nucleic acid sequence complementary to at least residues 519–1059 of SEQ ID NO: 1; wherein the first nucleic acid probe specifically hybridizes to a polynucleotide having a sequence as set forth in SEQ ID NO: 1 or 3 under conditions at least as stringent as at about room temperature in 2×SSC and 1% SDS with a subsequent wash step at about room temperature in 0.2×SSC and 0.1% SDS; and
- b) a second container containing a second nucleic acid probe comprising at least residues 519–1059 of SEQ ID NO: 1; or at least residues 519–1059 of SEQ ID NO: 1, wherein T is U; wherein the second nucleic acid probe specifically hybridizes to a polynucleotide having a sequence complementary to SEQ ID NO: 1 or 3 under conditions at least as stringent as at about room temperature in 2×SSC and 1% SDS with a subsequent wash step at about room temperature in 0.2×SSC and 0.1% SDS.

15. An isolated polynucleotide having a nucleotide sequence consisting essentially of at least the contiguous nucleotide bases of residues 519–1059 of SEQ ID NO: 1 or 3; residues 519–1059 of SEQ ID NO: 1 or 3, wherein T is U; a nucleotide sequence complementary to residues 519–1059 of SEQ ID NO: 1 or 3; or a nucleotide sequence complementary to residues 519–1059 of SEQ ID NO: 1 or 3, wherein T is U.

16. The kit of claim 11, wherein the nucleic acid probe specifically hybridizes under conditions at least as stringent as at about room temperature in 2×SSC and 1% SDS with a subsequent wash step at about 42° C. in 0.2×SSC and 0.1% SDS.

17. The kit of claim 11, wherein the nucleic acid probe specifically hybridizes under conditions at least as stringent as at about room temperature in 2×SSC and 1% SDS with a subsequent wash step at about 68° C. in 0.1×SSC.

18. The kit of claim 14, wherein the first nucleic acid probe and the second nucleic acid probe specifically hybridize under conditions at least as stringent as at about room temperature in 2×SSC and 1% SDS with a subsequent wash step at about 42° C. in 0.2×SSC and 0.1% SDS.

19. The kit of claim 14, wherein the first nucleic acid probe and the second nucleic acid probe specifically hybridize under conditions at least as stringent as at about room temperature in 2×SSC and 1% SDS with a subsequent wash step at about 68° C. in 0.1×SSC.

20. An isolated polynucleotide encoding a polypeptide comprising the amino acid sequence of SEQ ID NO: 2 or SEQ ID NO: 4.

21. A vector comprising the polynucleotide of claim 20.

22. A host cell comprising the vector of claim 21.

23. A method for producing an ABC7 polypeptide comprising:
- a) growing a host cell comprising the isolated polynucleotide of claim 20 under conditions which allow expression of the encoded polypeptide; and
- b) isolating the polypeptide.

* * * * *

UNITED STATES PATENT AND TRADEMARK OFFICE
CERTIFICATE OF CORRECTION

PATENT NO.   : 6,867,017 B1
DATED        : March 15, 2005
INVENTOR(S)  : Dean et al.

It is certified that error appears in the above-identified patent and that said Letters Patent is hereby corrected as shown below:

Column 3,
Line 54, "oh" should read -- on --.

Column 6,
Line 27, "5.3705" should read -- 53705 --.
Line 27, "BANTDS" should read -- BANDS --.
Line 36, "CLUSTAL.V" should read -- CLUSTAL V --.

Column 8,
Line 55, "transform." should read -- transform --.

Column 12,
Line 19, "106,1991." should read -- 106, 1991. --.

Column 15,
Line 62, "efficient" should read -- sufficient --.

Column 18,
Line 40, "Bioiechniques" should read -- Biotechniques --.

Column 19,
Line 51, "thereof" should read -- thereof. --.

Column 24,
Line 51, "72°C.," should read -- 72°C., 30 sec. PCR --.

Column 25,
Line 40, "certainty)" should read -- certainty --.
Line 63, "Glayac" should read -- Glavac --.

UNITED STATES PATENT AND TRADEMARK OFFICE
CERTIFICATE OF CORRECTION

PATENT NO. : 6,867,017 B1
DATED : March 15, 2005
INVENTOR(S) : Dean et al.

It is certified that error appears in the above-identified patent and that said Letters Patent is hereby corrected as shown below:

Column 26,
Lines 27 and 38, "1395M" should read -- I395M --.

Column 26, line 62 through Column 27, line 3,
"0.4 mM $CuCl_2$ ... the mutant atm1 strain" should be deleted as duplicative of text at Column 26, line 54 through Column 26, line 62.

Signed and Sealed this

Eleventh Day of April, 2006

JON W. DUDAS
*Director of the United States Patent and Trademark Office*

SEQUENCE LISTING

<160> NUMBER OF SEQ ID NOS: 6

<210> SEQ ID NO 1
<211> LENGTH: 2345
<212> TYPE: DNA
<213> ORGANISM: Homo sapien

<400> SEQUENCE: 1

```
atggcgctgc tcgcgatgca ttcttggcgc tgggcggccg cggcggctgc tttcgaaaag      60
cgccggcact ccgcgattct gatccggcct ttagtctctg ttagcggctc aggtccgcag     120
tggaggccac atcaactcgg cgccttggga accgctcgag cctaccagat tccagagtca     180
ttaaaaagta tcacatggca gagattggga aaaggcaatt caggacagtt cttagatgct     240
gcaaaggctc tccaggtatg gccactgata gaaaagagga catgttggca tggtcatgca     300
ggaggaggac tccacacaga cccaaaagaa gggttaaaag atgttgatac tcggaaaatc     360
ataaaagcaa tgctttctta tgtgtggccc aaagacaggc cagatctacg agctagagtt     420
gccatttcgc tgggattttt gggtggtgca aaggccatga atattgtggt tcccttcatg     480
tttaaatatg ctgtagacag cctcaaccag atgtcgggaa acatgctgaa cctgagtgat     540
gcaccaaata cagttgcaac catggcaaca gcagttctga ttggctatgg tgtatcaaga     600
gctggagctg cttttttttaa cgaagttcga aatgcagtat ttggcaaggt agcccagaat     660
tcaatccgaa gaatagccaa aaatgtcttt ctccatcttc acaacctgga tctgggtttt     720
```

-continued

```
cacctgagca gacagacggg agctttatct aaggctattg acagaggaac aaagggtatc      780
agttttgtcc tgagtgcttt ggtatttaat cttcttccca tcatgtttga agtgatgctt      840
gtcagtggtg ttttgtatta caaatgcggt gcccagtttg cttggtaac ccttggaaca       900
cttggtacat acacagcatt cacagttgca gtcacacggt ggagaactag atttagaata      960
gaaatgaaca aagcagataa tgatgcaggt aatgctgcta tagactcact gctgaattat     1020
gaaactgtga agtatttaa taatgaaaga tatgaagcac agagatatga tggattttg      1080
aagacgtatg agactgcttc attgaaaagt acctctactc tggctatgct gaactttggt     1140
caaagtgcta ttttcagtgt cggtttaaca gctataatgg tgctcgccag tcagggaatt     1200
gtggcaggta cccttactgt tggagatcta gtaatggtga atggactgct ttttcagctt     1260
tcattacccc tgaactttct gggaactgta tatagagaga ctagacaagc actcatagat     1320
atgaacacct tgtttactct actcaaggta gacacccaaa ttaaagacaa agtgatggca     1380
tctccccttc agatcacacc acagacagct accgtggcct ttgataatgt gcattttgaa     1440
tacattgagg gccagaaagt ccttagtgga atatcctttg aagtccctgc aggaaagaaa     1500
gtggccattg taggaggtag tgggtcaggg aaaagcacaa tagtgaggct attatttcgc     1560
ttctatgagc ctcaaaaggg tagcatttat cttgctggtc aaaatataca agatgtgagc     1620
ctggaaagcc ttcggagggc agtgggagtg gtacctcagg atgctgtcct cttccataat     1680
actatttatt acaacctctt atatggaaac atcagtgctt cacctgagga agtgtatgca     1740
gtggcaaaat tagctggact tcatgatgca attcttcgaa tgccacatgg atatgacacc     1800
caagtagggg aacgaggact caagcttca ggaggagaaa agcaaagagt agcaattgca     1860
agagccattt tgaaggaccc cccagtcata ctctatgatg aagctacttc atcgttagat     1920
tcgattactg aagagactat tcttggtgcc atgaaggatg tggtcaaaca cagaacttct     1980
attttcattg cacacagatt gtcaacagtg gttgatgcag atgaaatcat tgtcttggat     2040
cagggtaagg tagccgaacg tggtacccac catggtttgc ttgctaaccc tcatagtatc     2100
tattcagaaa tgtggcatac acagagcagc cgtgtgcaga accatgataa ccccaaatgg     2160
gaagcaaaga aagaaaatat atccaaagag gaggaaagaa agaaactaca agaagaaatt     2220
gtcaatagtg tgaaaggctg tggaaactgt tcgtgctaag tcacataaga catttctttt     2280
ttttgttgtt ttggactaca tatttgcact gaagcagaat tgttttatta aaaaaatcat     2340
acatt                                                                 2345
```

<210> SEQ ID NO 2
<211> LENGTH: 747
<212> TYPE: PRT
<213> ORGANISM: Homo sapien

<400> SEQUENCE: 2

```
Met His Ser Trp Arg Trp Ala Ala Ala Ala Ala Phe Glu Lys Arg
1               5                   10                  15

Arg His Ser Ala Ile Leu Ile Arg Pro Leu Val Ser Val Ser Gly Ser
            20                  25                  30

Gly Pro Gln Trp Arg Pro His Gln Leu Gly Ala Leu Gly Thr Ala Arg
        35                  40                  45

Ala Tyr Gln Ile Pro Glu Ser Leu Lys Ser Ile Thr Trp Gln Arg Leu
    50                  55                  60

Gly Lys Gly Asn Ser Gly Gln Phe Leu Asp Ala Ala Lys Ala Leu Gln
65                  70                  75                  80
```

-continued

```
Val Trp Pro Leu Ile Glu Lys Arg Thr Cys Trp His Gly His Ala Gly
                 85                  90                  95

Gly Gly Leu His Thr Asp Pro Lys Glu Gly Leu Lys Asp Val Asp Thr
            100                 105                 110

Arg Lys Ile Ile Lys Ala Met Leu Ser Tyr Val Trp Pro Lys Asp Arg
        115                 120                 125

Pro Asp Leu Arg Ala Arg Val Ala Ile Ser Leu Gly Phe Leu Gly Gly
    130                 135                 140

Ala Lys Ala Met Asn Ile Val Val Pro Phe Met Phe Lys Tyr Ala Val
145                 150                 155                 160

Asp Ser Leu Asn Gln Met Ser Gly Asn Met Leu Asn Leu Ser Asp Ala
                165                 170                 175

Pro Asn Thr Val Ala Thr Met Ala Thr Ala Val Leu Ile Gly Tyr Gly
            180                 185                 190

Val Ser Arg Ala Gly Ala Ala Phe Phe Asn Glu Val Arg Asn Ala Val
        195                 200                 205

Phe Gly Lys Val Ala Gln Asn Ser Ile Arg Arg Ile Ala Lys Asn Val
    210                 215                 220

Phe Leu His Leu His Asn Leu Asp Leu Gly Phe His Leu Ser Arg Gln
225                 230                 235                 240

Thr Gly Ala Leu Ser Lys Ala Ile Asp Arg Gly Thr Lys Gly Ile Ser
                245                 250                 255

Phe Val Leu Ser Ala Leu Val Phe Asn Leu Leu Pro Ile Met Phe Glu
            260                 265                 270

Val Met Leu Val Ser Gly Val Leu Tyr Tyr Lys Cys Gly Ala Gln Phe
        275                 280                 285

Ala Leu Val Thr Leu Gly Thr Leu Gly Thr Tyr Thr Ala Phe Thr Val
    290                 295                 300

Ala Val Thr Arg Trp Arg Thr Arg Phe Arg Ile Glu Met Asn Lys Ala
305                 310                 315                 320

Asp Asn Asp Ala Gly Asn Ala Ala Ile Asp Ser Leu Leu Asn Tyr Glu
                325                 330                 335

Thr Val Lys Tyr Phe Asn Asn Glu Arg Tyr Glu Ala Gln Arg Tyr Asp
            340                 345                 350

Gly Phe Leu Lys Thr Tyr Glu Thr Ala Ser Leu Lys Ser Thr Ser Thr
        355                 360                 365

Leu Ala Met Leu Asn Phe Gly Gln Ser Ala Ile Phe Ser Val Gly Leu
    370                 375                 380

Thr Ala Ile Met Val Leu Ala Ser Gln Gly Ile Val Ala Gly Thr Leu
385                 390                 395                 400

Thr Val Gly Asp Leu Val Met Val Asn Gly Leu Leu Phe Gln Leu Ser
                405                 410                 415

Leu Pro Leu Asn Phe Leu Gly Thr Val Tyr Arg Glu Thr Arg Gln Ala
            420                 425                 430

Leu Ile Asp Met Asn Thr Leu Phe Thr Leu Lys Val Asp Thr Gln
    435                 440                 445

Ile Lys Asp Lys Val Met Ala Ser Pro Leu Gln Ile Thr Pro Gln Thr
450                 455                 460

Ala Thr Val Ala Phe Asp Asn Val His Phe Glu Tyr Ile Glu Gly Gln
465                 470                 475                 480

Lys Val Leu Ser Gly Ile Ser Phe Glu Val Pro Ala Gly Lys Lys Val
                485                 490                 495
```

-continued

Ala Ile Val Gly Gly Ser Gly Ser Gly Lys Ser Thr Ile Val Arg Leu
        500             505             510

Leu Phe Arg Phe Tyr Glu Pro Gln Lys Gly Ser Ile Tyr Leu Ala Gly
        515             520             525

Gln Asn Ile Gln Asp Val Ser Leu Glu Ser Leu Arg Arg Ala Val Gly
        530             535             540

Val Val Pro Gln Asp Ala Val Leu Phe His Asn Thr Ile Tyr Tyr Asn
545             550             555             560

Leu Leu Tyr Gly Asn Ile Ser Ala Ser Pro Glu Val Tyr Ala Val
            565             570             575

Ala Lys Leu Ala Gly Leu His Asp Ala Ile Leu Arg Met Pro His Gly
        580             585             590

Tyr Asp Thr Gln Val Gly Glu Arg Gly Leu Lys Leu Ser Gly Gly Glu
        595             600             605

Lys Gln Arg Val Ala Ile Ala Arg Ala Ile Leu Lys Asp Pro Pro Val
        610             615             620

Ile Leu Tyr Asp Glu Ala Thr Ser Ser Leu Asp Ser Ile Thr Glu Glu
625             630             635             640

Thr Ile Leu Gly Ala Met Lys Asp Val Val Lys His Arg Thr Ser Ile
            645             650             655

Phe Ile Ala His Arg Leu Ser Thr Val Val Asp Ala Asp Glu Ile Ile
        660             665             670

Val Leu Asp Gln Gly Lys Val Ala Glu Arg Gly Thr His His Gly Leu
        675             680             685

Leu Ala Asn Pro His Ser Ile Tyr Ser Glu Met Trp His Thr Gln Ser
        690             695             700

Ser Arg Val Gln Asn His Asp Asn Pro Lys Trp Glu Ala Lys Lys Glu
705             710             715             720

Asn Ile Ser Lys Glu Glu Arg Lys Lys Leu Gln Glu Glu Ile Val
            725             730             735

Asn Ser Val Lys Gly Cys Gly Asn Cys Ser Cys
        740             745

<210> SEQ ID NO 3
<211> LENGTH: 2345
<212> TYPE: DNA
<213> ORGANISM: Homo sapien

<400> SEQUENCE: 3
atggcgctgc tcgcgatgca ttcttggcgc tgggcggccg cggcggctgc tttcgaaaag      60
cgccggcact ccgcgattct gatccggcct ttagtctctg ttagcggctc aggtccgcag     120
tggaggccac atcaactcgg cgccttggga accgctcgag cctaccagat tccagagtca     180
ttaaaaagta tcacatggca gagattggga aaaggcaatt caggacagtt cttagatgct     240
gcaaaggctc tccaggtatg gccactgata gaaagagga catgttggca tggtcatgca     300
ggaggaggac tccacacaga cccaaaagaa gggttaaaag atgttgatac tcggaaaatc     360
ataaaagcaa tgctttctta tgtgtggccc aaagacaggc cagatctacg agctagagtt     420
gccatttcgc tgggattttt gggtggtgca aaggccatga atattgtggt tcccttcatg     480
tttaaatatg ctgtagacag cctcaaccag atgtcgggaa acatgctgaa cctgagtgat     540
gcaccaaata cagttgcaac catggcaaca gcagttctga ttggctatgg tgtatcaaga     600
gctggagctg cttttttaa cgaagttcga aatgcagtat ttggcaaggt agcccagaat     660
tcaatccgaa gaatagccaa aaatgtctt ctccatcttc acaacctgga tctgggtttt     720

-continued

```
cacctgagca gacagacggg agctttatct aaggctattg acagaggaac aaagggtatc    780
agttttgtcc tgagtgcttt ggtatttaat cttcttccca tcatgtttga agtgatgctt    840
gtcagtggtg ttttgtatta caaatgcggt gcccagtttg cttggtaac ccttggaaca     900
cttggtacat acacagcatt cacagttgca gtcacacggt ggagaactag atttagaata    960
gaaatgaaca aagcagataa tgatgcaggt aatgctgcta tagactcact gctgaattat   1020
gaaactgtga agtattttaa taatgaaaga tatgaagcac agagatatga tggattttg    1080
aagacgtatg agactgcttc attgaaaagt acctctactc tggctatgct gaactttggt   1140
caaagtgcta ttttcagtgt cggtttaaca gctataatgg tgctcgccag tcagggaatg   1200
gtggcaggta cccttactgt tggagatcta gtaatggtga atggactgct ttttcagctt   1260
tcattacccc tgaactttct gggaactgta tatagagaga ctagacaagc actcatagat   1320
atgaacacct tgtttactct actcaaggta gacacccaaa ttaaagacaa agtgatggca   1380
tctcccttc agatcacacc acagacagct accgtggcct ttgataatgt gcattttgaa    1440
tacattgagg gccagaaagt ccttagtgga atatcctttg aagtccctgc aggaaagaaa   1500
gtggccattg taggaggtag tgggtcaggg aaaagcacaa tagtgaggct attatttcgc   1560
ttctatgagc ctcaaaaggg tagcatttat cttgctggtc aaaatataca agatgtgagc   1620
ctggaaagcc ttcggagggc agtgggagtg gtacctcagg atgctgtcct cttccataat   1680
actatttatt acaacctctt atatggaaac atcagtgctt cacctgagga agtgtatgca   1740
gtggcaaaat tagctggact tcatgatgca attcttcgaa tgccacatgg atatgacacc   1800
caagtagggg aacgaggact caagcttttca ggaggagaaa agcaaagagt agcaattgca   1860
agagccattt tgaaggaccc cccagtcata ctctatgatg aagctacttc atcgttagat   1920
tcgattactg aagagactat tcttggtgcc atgaaggatg tggtcaaaca cagaacttct   1980
attttcattg cacacagatt gtcaacagtg gttgatgcag atgaaatcat tgtcttggat   2040
cagggtaagg tagccgaacg tggtacccac catggttttgc ttgctaaccc tcatagtatc   2100
tattcagaaa tgtggcatac acagagcagc cgtgtgcaga accatgataa ccccaaatgg   2160
gaagcaaaga aagaaaatat atccaaagag gaggaaagaa agaaactaca agaagaaatt   2220
gtcaatagtg tgaaaggctg tggaaactgt tcgtgctaag tcacataaga catttttctt   2280
ttttgttgtt ttggactaca tatttgcact gaagcagaat tgtttatta aaaaaatcat   2340
acatt                                                              2345
```

<210> SEQ ID NO 4
<211> LENGTH: 747
<212> TYPE: PRT
<213> ORGANISM: Homo sapien

<400> SEQUENCE: 4

Met His Ser Trp Arg Trp Ala Ala Ala Ala Ala Phe Glu Lys Arg
1               5                   10                  15

Arg His Ser Ala Ile Leu Ile Arg Pro Leu Val Ser Val Ser Gly Ser
            20                  25                  30

Gly Pro Gln Trp Arg Pro His Gln Leu Gly Ala Leu Gly Thr Ala Arg
        35                  40                  45

Ala Tyr Gln Ile Pro Glu Ser Leu Lys Ser Ile Thr Trp Gln Arg Leu
    50                  55                  60

Gly Lys Gly Asn Ser Gly Gln Phe Leu Asp Ala Lys Ala Leu Gln
65                  70                  75                  80

-continued

```
Val Trp Pro Leu Ile Glu Lys Arg Thr Cys Trp His Gly His Ala Gly
                 85                  90                  95

Gly Gly Leu His Thr Asp Pro Lys Glu Gly Leu Lys Asp Val Asp Thr
                100                 105                 110

Arg Lys Ile Ile Lys Ala Met Leu Ser Tyr Val Trp Pro Lys Asp Arg
                115                 120                 125

Pro Asp Leu Arg Ala Arg Val Ala Ile Ser Leu Gly Phe Leu Gly Gly
            130                 135                 140

Ala Lys Ala Met Asn Ile Val Val Pro Phe Met Phe Lys Tyr Ala Val
145                 150                 155                 160

Asp Ser Leu Asn Gln Met Ser Gly Asn Met Leu Asn Leu Ser Asp Ala
                165                 170                 175

Pro Asn Thr Val Ala Thr Met Ala Thr Ala Val Leu Ile Gly Tyr Gly
                180                 185                 190

Val Ser Arg Ala Gly Ala Ala Phe Phe Asn Glu Val Arg Asn Ala Val
            195                 200                 205

Phe Gly Lys Val Ala Gln Asn Ser Ile Arg Arg Ile Ala Lys Asn Val
            210                 215                 220

Phe Leu His Leu His Asn Leu Asp Leu Gly Phe His Leu Ser Arg Gln
225                 230                 235                 240

Thr Gly Ala Leu Ser Lys Ala Ile Asp Arg Gly Thr Lys Gly Ile Ser
                245                 250                 255

Phe Val Leu Ser Ala Leu Val Phe Asn Leu Leu Pro Ile Met Phe Glu
                260                 265                 270

Val Met Leu Val Ser Gly Val Leu Tyr Tyr Lys Cys Gly Ala Gln Phe
            275                 280                 285

Ala Leu Val Thr Leu Gly Thr Leu Gly Thr Tyr Thr Ala Phe Thr Val
            290                 295                 300

Ala Val Thr Arg Trp Arg Thr Arg Phe Arg Ile Glu Met Asn Lys Ala
305                 310                 315                 320

Asp Asn Asp Ala Gly Asn Ala Ala Ile Asp Ser Leu Leu Asn Tyr Glu
                325                 330                 335

Thr Val Lys Tyr Phe Asn Asn Glu Arg Tyr Glu Ala Gln Arg Tyr Asp
                340                 345                 350

Gly Phe Leu Lys Thr Tyr Glu Thr Ala Ser Leu Lys Ser Thr Ser Thr
            355                 360                 365

Leu Ala Met Leu Asn Phe Gly Gln Ser Ala Ile Phe Ser Val Gly Leu
            370                 375                 380

Thr Ala Ile Met Val Leu Ala Ser Gln Gly Met Val Ala Gly Thr Leu
385                 390                 395                 400

Thr Val Gly Asp Leu Val Met Val Asn Gly Leu Leu Phe Gln Leu Ser
                405                 410                 415

Leu Pro Leu Asn Phe Leu Gly Thr Val Tyr Arg Glu Thr Arg Gln Ala
            420                 425                 430

Leu Ile Asp Met Asn Thr Leu Phe Thr Leu Leu Lys Val Asp Thr Gln
            435                 440                 445

Ile Lys Asp Lys Val Met Ala Ser Pro Leu Gln Ile Thr Pro Gln Thr
450                 455                 460

Ala Thr Val Ala Phe Asp Asn Val His Phe Glu Tyr Ile Glu Gly Gln
465                 470                 475                 480

Lys Val Leu Ser Gly Ile Ser Phe Glu Val Pro Ala Gly Lys Lys Val
                485                 490                 495
```

-continued

```
Ala Ile Val Gly Gly Ser Gly Ser Gly Lys Ser Thr Ile Val Arg Leu
            500                 505                 510

Leu Phe Arg Phe Tyr Glu Pro Gln Lys Gly Ser Ile Tyr Leu Ala Gly
        515                 520                 525

Gln Asn Ile Gln Asp Val Ser Leu Glu Ser Leu Arg Arg Ala Val Gly
    530                 535                 540

Val Val Pro Gln Asp Ala Val Leu Phe His Asn Thr Ile Tyr Tyr Asn
545                 550                 555                 560

Leu Leu Tyr Gly Asn Ile Ser Ala Ser Pro Glu Val Tyr Ala Val
            565                 570                 575

Ala Lys Leu Ala Gly Leu His Asp Ala Ile Leu Arg Met Pro His Gly
            580                 585                 590

Tyr Asp Thr Gln Val Gly Glu Arg Gly Leu Lys Leu Ser Gly Gly Glu
        595                 600                 605

Lys Gln Arg Val Ala Ile Ala Arg Ala Ile Leu Lys Asp Pro Pro Val
    610                 615                 620

Ile Leu Tyr Asp Glu Ala Thr Ser Ser Leu Asp Ser Ile Thr Glu Glu
625                 630                 635                 640

Thr Ile Leu Gly Ala Met Lys Asp Val Val Lys His Arg Thr Ser Ile
            645                 650                 655

Phe Ile Ala His Arg Leu Ser Thr Val Val Asp Ala Asp Glu Ile Ile
            660                 665                 670

Val Leu Asp Gln Gly Lys Val Ala Glu Arg Gly Thr His His Gly Leu
        675                 680                 685

Leu Ala Asn Pro His Ser Ile Tyr Ser Glu Met Trp His Thr Gln Ser
        690                 695                 700

Ser Arg Val Gln Asn His Asp Asn Pro Lys Trp Glu Ala Lys Lys Glu
705                 710                 715                 720

Asn Ile Ser Lys Glu Glu Arg Lys Lys Leu Gln Glu Glu Ile Val
            725                 730                 735

Asn Ser Val Lys Gly Cys Gly Asn Cys Ser Cys
            740                 745

<210> SEQ ID NO 5
<211> LENGTH: 23
<212> TYPE: DNA
<213> ORGANISM: Artificial Sequence
<220> FEATURE:
<223> OTHER INFORMATION: Reverse Primer

<400> SEQUENCE: 5
tgcttcagtg caaatatgta gtc                                        23

<210> SEQ ID NO 6
<211> LENGTH: 690
<212> TYPE: PRT
<213> ORGANISM: Saccharomyces cerevisiae

<400> SEQUENCE: 6

Met Leu Leu Leu Pro Arg Cys Pro Val Ile Gly Arg Ile Val Arg Ser
1               5                   10                  15

Lys Phe Arg Ser Gly Leu Ile Arg Asn His Ser Pro Val Ile Phe Thr
            20                  25                  30

Val Ser Lys Leu Ser Thr Gln Arg Pro Leu Leu Phe Asn Ser Ala Val
        35                  40                  45

Asn Leu Trp Asn Gln Ala Gln Lys Asp Ile Thr His Lys Lys Ser Val
    50                  55                  60
```

-continued

```
Glu Gln Phe Ser Ser Ala Pro Lys Val Lys Thr Gln Val Lys Thr
 65                  70                  75                  80

Ser Lys Ala Pro Thr Leu Ser Glu Leu Lys Ile Leu Lys Asp Leu Phe
                 85                  90                  95

Arg Tyr Ile Trp Pro Lys Gly Asn Asn Lys Val Arg Ile Arg Val Leu
                100                 105                 110

Ile Ala Leu Gly Leu Leu Ile Ser Ala Lys Ile Leu Asn Val Gln Val
            115                 120                 125

Pro Phe Phe Phe Lys Gln Thr Ile Asp Ser Met Asn Ile Ala Trp Asp
130                 135                 140

Asp Pro Thr Val Ala Leu Pro Ala Ala Ile Gly Leu Thr Ile Leu Cys
145                 150                 155                 160

Tyr Gly Val Ala Arg Phe Gly Ser Val Leu Phe Gly Glu Leu Arg Asn
                165                 170                 175

Ala Val Phe Ala Lys Val Ala Gln Asn Ala Ile Arg Thr Val Ser Leu
            180                 185                 190

Gln Thr Phe Gln His Leu Met Lys Leu Asp Leu Gly Trp His Leu Ser
        195                 200                 205

Arg Gln Thr Gly Gly Leu Thr Arg Ala Met Asp Arg Gly Thr Lys Gly
210                 215                 220

Ile Ser Gln Val Leu Thr Ala Met Val Phe His Ile Ile Pro Ile Ser
225                 230                 235                 240

Phe Glu Ile Ser Val Val Cys Gly Ile Leu Thr Tyr Gln Phe Gly Ala
                245                 250                 255

Ser Phe Ala Ala Ile Thr Phe Ser Thr Met Leu Leu Tyr Ser Ile Phe
            260                 265                 270

Thr Ile Lys Thr Thr Ala Trp Arg Thr His Phe Arg Arg Asp Ala Asn
        275                 280                 285

Lys Ala Asp Asn Lys Ala Ala Ser Val Ala Leu Asp Ser Leu Ile Asn
290                 295                 300

Phe Glu Ala Val Lys Tyr Phe Asn Asn Glu Lys Tyr Leu Ala Asp Lys
305                 310                 315                 320

Tyr Asn Gly Ser Leu Met Asn Tyr Arg Asp Ser Gln Ile Lys Val Ser
                325                 330                 335

Gln Ser Leu Ala Phe Leu Asn Ser Gly Gln Asn Leu Ile Phe Thr Thr
            340                 345                 350

Ala Leu Thr Ala Met Met Tyr Met Gly Cys Thr Gly Val Ile Gly Gly
        355                 360                 365

Asn Leu Thr Val Gly Asp Leu Val Leu Ile Asn Gln Leu Val Phe Gln
370                 375                 380

Leu Ser Val Pro Leu Asn Phe Leu Gly Ser Val Tyr Arg Asp Leu Lys
385                 390                 395                 400

Gln Ser Leu Ile Asp Met Glu Thr Leu Phe Lys Leu Arg Lys Asn Glu
                405                 410                 415

Val Lys Ile Lys Asn Ala Glu Arg Pro Leu Met Leu Pro Glu Asn Val
            420                 425                 430

Pro Tyr Asp Ile Thr Phe Glu Asn Val Thr Phe Gly Tyr His Pro Asp
        435                 440                 445

Arg Lys Ile Leu Lys Asn Ala Ser Phe Thr Ile Pro Ala Gly Trp Lys
    450                 455                 460

Thr Ala Ile Val Gly Ser Ser Gly Ser Gly Lys Ser Thr Ile Leu Lys
465                 470                 475                 480
```

-continued

```
Leu Val Phe Arg Phe Tyr Asp Pro Glu Ser Gly Arg Ile Leu Ile Asn
            485                 490                 495

Gly Arg Asp Ile Lys Glu Tyr Asp Ile Asp Ala Leu Arg Lys Val Ile
            500                 505                 510

Gly Val Val Pro Gln Asp Thr Pro Leu Phe Asn Asp Thr Ile Trp Glu
            515                 520                 525

Asn Val Lys Phe Gly Arg Ile Asp Ala Thr Asp Glu Glu Val Ile Thr
        530                 535                 540

Val Val Glu Lys Ala Gln Leu Ala Pro Leu Ile Lys Lys Leu Pro Gln
545                 550                 555                 560

Gly Phe Asp Thr Ile Val Gly Glu Arg Gly Leu Met Ile Ser Gly Gly
                565                 570                 575

Glu Lys Gln Arg Leu Ala Ile Ala Arg Val Leu Leu Lys Asn Ala Arg
                580                 585                 590

Ile Met Phe Phe Asp Glu Ala Thr Ser Ala Leu Asp Thr His Thr Glu
                595                 600                 605

Gln Ala Leu Leu Arg Thr Ile Arg Asp Asn Phe Thr Ser Gly Ser Arg
        610                 615                 620

Thr Ser Val Tyr Ile Ala His Arg Leu Arg Thr Ile Ala Asp Ala Asp
625                 630                 635                 640

Lys Ile Ile Val Leu Asp Asn Gly Arg Val Arg Glu Glu Gly Lys His
                645                 650                 655

Leu Glu Leu Leu Ala Met Pro Gly Ser Leu Tyr Arg Glu Leu Trp Thr
                660                 665                 670

Ile Gln Glu Asp Leu Asp His Leu Glu Asn Glu Leu Lys Asp Gln Gln
            675                 680                 685

Glu Leu
    690
```